(12) United States Patent
Ladel et al.

(10) Patent No.: US 12,332,250 B2
(45) Date of Patent: *Jun. 17, 2025

(54) INFLAMMATORY BIOMARKERS FOR PREDICTING RESPONSIVENESS TO FGF-18 COMPOUND

(71) Applicant: MERCK PATENT GMBH, Darmstadt (DE)

(72) Inventors: Christoph H. Ladel, Darmstadt (DE); Hans Guehring, Geisenheim (DE); Anne-Christine Bay-Jensen, Copenhagen (DK); Morten Karsdal, Copenhagen (DK); Per Qvist, Copenhagen (DK)

(73) Assignee: Merck Patent GmbH, Darmstadt (DE)

( * ) Notice: Subject to any disclaimer, the term of this patent is extended or adjusted under 35 U.S.C. 154(b) by 58 days.

This patent is subject to a terminal disclaimer.

(21) Appl. No.: 17/929,261

(22) Filed: Sep. 1, 2022

(65) Prior Publication Data

US 2023/0258659 A1    Aug. 17, 2023

Related U.S. Application Data

(63) Continuation of application No. 16/650,878, filed as application No. PCT/EP2018/076391 on Sep. 28, 2018, now Pat. No. 11,467,169.

(30) Foreign Application Priority Data

Sep. 29, 2017 (EP) ..................... 17194169
Apr. 25, 2018 (EP) ..................... 18169317

(51) Int. Cl.
*G01N 33/68* (2006.01)
*A61K 38/18* (2006.01)
*A61P 19/04* (2006.01)

(52) U.S. Cl.
CPC ..... *G01N 33/6887* (2013.01); *A61K 38/1825* (2013.01); *A61P 19/04* (2018.01); *G01N 2800/10* (2013.01); *G01N 2800/52* (2013.01)

(58) Field of Classification Search
None
See application file for complete search history.

(56) References Cited

U.S. PATENT DOCUMENTS

| | | |
|---|---|---|
| 8,207,115 B2 | 6/2012 | Gimona et al. |
| 9,326,944 B2 | 5/2016 | Cerreti et al. |
| 9,724,388 B2 | 8/2017 | Ladel et al. |
| 9,795,714 B2 | 10/2017 | Canal et al. |
| 9,889,179 B2 | 2/2018 | Ladel et al. |
| 10,086,112 B2 | 10/2018 | Ladel et al. |
| 10,221,456 B2 | 3/2019 | Ladel et al. |
| 10,293,051 B2 | 5/2019 | Lo Presti et al. |
| 11,467,169 B2 | 10/2022 | Ladel et al. |
| 11,513,128 B2 | 11/2022 | Ladel et al. |
| 2007/0207480 A1 | 9/2007 | Gobezie |
| 2007/0292892 A1 | 12/2007 | Sandell et al. |
| 2009/0299769 A1 | 12/2009 | Dam et al. |
| 2010/0016223 A1 | 1/2010 | Gimona et al. |
| 2010/0098775 A1 | 4/2010 | Bukowski et al. |
| 2012/0115137 A1 | 5/2012 | Kornman et al. |
| 2015/0203592 A1 | 7/2015 | Wang |
| 2015/0218637 A1 | 8/2015 | Ladel et al. |
| 2017/0299611 A1 | 10/2017 | Ruff |
| 2019/0161801 A1 | 5/2019 | Ladel et al. |
| 2021/0231680 A1 | 7/2021 | Ladel et al. |
| 2021/0231681 A1 | 7/2021 | Ladel et al. |
| 2022/0047674 A1 | 2/2022 | Ladel et al. |
| 2023/0251271 A1 | 8/2023 | Ladel et al. |

FOREIGN PATENT DOCUMENTS

| | | |
|---|---|---|
| CN | 104736723 A | 6/2015 |
| CN | 108472290 A | 8/2018 |
| JP | 2009-257842 A | 11/2009 |
| WO | WO-1998/016644 A1 | 4/1998 |
| WO | WO-2004/032849 A2 | 4/2004 |
| WO | WO-2006/063362 A1 | 6/2006 |
| WO | WO-2008/023063 A2 | 2/2008 |
| WO | WO-2009/135218 A2 | 11/2009 |

(Continued)

OTHER PUBLICATIONS

Alaoui-Ismaili, M.H. and Falb, D., Design of second generation therapeutic recombinant bone morphogenetic proteins, Cytokine Growth Factor Rev., 20(5-6):501-507 (2009).

(Continued)

*Primary Examiner* — Elizabeth C. Kemmerer
(74) *Attorney, Agent, or Firm* — Choate, Hall & Stewart LLP; Michael A. Shinall; Stephany Foster

(57) ABSTRACT

The present invention relates to biomarkers associated with the clinical response to an FGF-18 compound before or during treatment of a cartilage disorder. It relates more particularly to specific proteins present in the blood, serum, synovial fluid or in the urine, which can be used as biomarkers for the diagnosis, pre-treatment of patients and during therapy of cartilage disorders. The invention can be used in predicting the response to an FGF-18 compound treatment, before starting the treatment or during the treatment. It could be used for selecting/identifying subjects to be treated according to specific doses and/or dosing regimens by intra-articular administration of an FGF-18 compound. The use of these biomarkers in diagnostics could result in increased benefit and reduced risk-benefit ratio in subjects.

13 Claims, 9 Drawing Sheets

Specification includes a Sequence Listing.

(56) References Cited

FOREIGN PATENT DOCUMENTS

| WO | WO-2012/172072 A1 | 12/2012 |
|---|---|---|
| WO | WO-2014/023703 A1 | 2/2014 |
| WO | WO-2014/023704 A1 | 2/2014 |
| WO | WO-2015/097233 A1 | 7/2015 |
| WO | WO-2015/097236 A2 | 7/2015 |
| WO | WO-2015/124731 A1 | 8/2015 |
| WO | WO-2015/124735 A1 | 8/2015 |
| WO | WO-2015/124739 A1 | 8/2015 |
| WO | WO-2016/120387 A1 | 8/2016 |
| WO | WO-2017/079765 A1 | 5/2017 |
| WO | WO-2019/063756 A1 | 4/2019 |
| WO | WO-2019/063758 A1 | 4/2019 |
| WO | WO-2020/053155 A1 | 3/2020 |

OTHER PUBLICATIONS

Attur, M. et al., 391 Association of Interleukin-1 receptor antagonist (IL-IRN) TTC Haplotype with radiographic knee OA severity in meta-analysis, Osteo. Cart., 18:S172 (2010).

Attur, M. et al., 392 Interleukin-1 receptor antagonist gene variations predict the severity and progression of knee osteoartritis, Osteo. Cart., 18:S172 (2010).

Bagger, Y.Z. et al., Oral salmon calcitonin induced suppression of urinary collagen type II degradation in postmenopausal women: a new potential treatment of osteoarthritis, Bone, 37(3):425-430 (2005).

Bay-Jensen, A.C. et al. Osteoarthritis Year in Review 2015: Soluble Biomarkers and the BIPED Criteria, Osteoarthritis Cartilage, 24(1):9-20 (2016).

Bay-Jensen, A.-C. et al., Elevated levels of CRPM, an inflammatory biomarker correlating with disease activity in RA, are prognostic of radiographic knee OA, Osteoarthritis and Cartilage, 25:S32 (2017).

Beers, M.H. et al., The Merck Manual of Diagnosis and Therapy, Merck, 17th edition, 7 pages, (1999).

Bellamy, N. et al. Validation Study of WOMAC: A Health Status Instrument for Measuring Clinically Important Patient Relevant Outcomes to Antirheumatic Drug Therapy in Patients with Osteoarthritis of the Hip or Knee. J. Rheumatol., 15(12):1933-1840 (1988).

Bhattacharya, R. et al., Impact of genetic variation on three dimensional structure and function of proteins, PLoS One, 12(3):e0171355 (2017).

Brittberg, M. et al. ICRS Cartilage Injury Evaluation Package, ICRS 2000 Standards Workshop, 16 Pages, (2000).

Buckland-Wright, J.C. et al., Quantitative microfocal radiography detects changes in OA knee joint space width in patients in placebo controlled trial of NSAID therapy, J. Rheumatol., 22(5):937-943 (1995).

Bukowski, J. et al., A49II-1RN Polymorphisms are associated with radiographic severity in osteoarthritis, osteo cartBukowski, J. et al., A49II-1RN Polymorphisms are associated with radiographic severity in osteoarthritis, Osteo. Cart., 16:S34 (2008).

Christgau, S. et al., Osteoarthritic patients with high cartilage turnover show increased responsiveness to the cartilage protecting effects of glucosamine sulphate, Clin. Exp. Rheumatol., 22(1):36-42 (2004).

Clinical Trial Protocol, Sprifermin Phase II Trial of Sprifermin in Knee OA EMR700692_006, Merck KGaA, Mar. 5, 2013, <https://clinicaltrials.gov/ProvidedDocs/64/NCT01919164/Prot_000.pdf>.

Dam, E. B. et al., Increased urinary excretion of C-telopeptides of type II collagen (CTX-II) predicts cartilage loss over 21 months by MRI, Osteoarthritis and Cartilage, 17(3):384-389 (2009).

Duclos, M.E. et al., Significance of the serum CTX-II level in an osteoarthritis animal model: a 5-month longitudinal study, Osteoarthritis Cartilage, 18(11):1467-1476 (2010).

Ellsworth, J. L. et al. Fibroblast Growth Factor-18 is a Trophic Factor for Mature Chondrocytes and Their Progenitors, Osteoarthritis Cartilage, 10(4):308-320 (2002).

Fenton, A.W. et al., Rheostat positions: A new classification of protein positions relevant to pharmacogenomics, Med. Chem. Res., 29(7):1133-1146 (2020).

Gigout, A. et al. Sprifermin (rhFGF18) Enables Proliferation of Chondrocytes Producing a Hyaline Cartilage Matrix, Osteoarthritis Cartilage, 25(11):1858-1867 (2017).

Grad, S. et al., Systemic blood plasma CCL5 and CXCL6: Potential biomarkers for human lumbar disc degeneration, Eur. Cell. Mater., 31:1-10 (2016).

Gudmann, N. S. et al., Chondrocyte Activity is Increased in Psoriatic Arthritis and Axial Spondyloarthritis. Arthritis Research & Therapy, 18(141):1-9 (2016).

Gudmann, N.S. et al., Cartilage Turnover Reflected by Metabolic Processing of Type II Collagen: A Novel Marker of Anabolic Function in Chondrocytes, Int. J. Mol. Sci., 15(10):18789-18803 (2014).

Guo, H.H. et al., Protein tolerance to random amino acid change, PNAS USA, 101(25):9205-9210 (2004).

Haque, T. et al., A Review of FGF18: Its Expression, Signaling Pathways and Possible Functions During Embryogenesis and Post-Natal Development, Histol Histopathol, 22(1):97-105 (2007).

Hosnijeh, F. S. et al., Association between biomarkers of tissue inflammation and progression of osteoarthritis: evidence from the Rotterdam study cohort, Arthritis Research Therapy, 18(81):1-10 (2016).

Jubb, R.W. et al., A one-year, randomised, placebo (saline) controlled clinical trial of 500-730 kDa sodium hyaluronate (Hyalgan) on the radiological change in osteoarthritis of the knee, Int. J. Clin. Pract., 57(6):467-474 (2003).

Karsdal, M.A. et al. Disease-Modifying Treatments for Osteoarthritis (DMOADs) of the Knee and Hip: Lessons Learned from Failures and Opportunities for the Future, Osteoarthritis Cartilage, 24(12):2013-2021 (2016).

Kerkhof, H.J.M. et a., Large-scale meta-analysis of interleukin-1 beta and interleukin-1 receptor antagonist polymorphisms on risk of radiographic hip and knee osteoarthritis and severity of knee osteoarthritis, Osteoarthr. Cartil., 19:265-271 (2011).

Krishnan, Y. and Grodzinsky, A.J. et al., Cartilage diseases, Matrix Biol., 71-72:51-69 (2018).

Liu, Z., Bone Mineral and Clinical Applications, China Sci. Tech. Press, 2 pages (2006).

Lotz, M.K., Posttraumatic Osteoarthritis: Pathogenesis and Pharmacological Treatment Options, Arthritis Res. Ther., 12(3):211 (2010).

Maijer, K.I. et al., Neo-Epitopes-Fragments of Cartilage and Connective Tissue Degradation in Early Rheumatoid Arthritis and Unclassed Arthritis, PLoS One, 11(3):e0149329 (2016).

Mazzuca, S.A. et al., Is conventional radiography suitable for evaluation of a disease-modifying drug in patients with knee osteoarthritis? Osteoarthritis Cartilage, 5(4):217-226 (1997).

Mori, Y. et al., Identification of Fibroblast Growth Factor-18 as a Molecule to Protect Adult Articular Cartilage by Gene Expression Profiling, The Journal of Biological Chemistry, 289(14):10192-10200 (2014).

Mummidi, S. et al., Evolution of Human and Non-human Primate CC Chemokine Receptor 5 Gene and mRNA, Jrnl. Biol. Chem., 275(25):18946-961 (2000).

Munk, H. L. et al., Cartilage Collagen Type II Seromarker Patterns in Axial Spondyloarthritis and Psoriatic Arthritis: Associations with Disease Activity, Smoking and HLA-B27, Rheumatology International, 36(4):541-549 (2016).

Reker, D. et al., Extracellular Matrix Changes in Response to Sprifermin Studied in Ex Vivo Cultures of Aricular Cartilage, Abstract, Osteoarthritis and Cartilage, 206:A142-A143 (2015).

Reker, D. et al., Sprifermin (rhFGF18) modulates extracellular matrix turnover in cartilage explants ex vivo, J. Transl. Med., 15:1-12 (2017).

Rowshan, H.H. et al., Pseudomonas aeruginosa infection of the auricular cartilage caused by "high ear piercing": a case report and review of the literature, J. Oral. Maxillofac. Surg., 66(3):543-546 (2008).

Sawitzke, A.D. et al., The effect of glucosamine and/or chondroitin sulfate on the progression of knee osteoarthritis: a GAIT report, Arthritis Rheum., 58(10):3183-3191 (2008).

Sherwood, J. et al., A homeostatic function of CXCR2 signalling in articular cartilage, Ann. Rheum. Dis., 74(12):2207-2215 (2015).

(56) References Cited

OTHER PUBLICATIONS

Shimoaka, T. et al. Regulation of Osteoblast, Chondrocyte, and Osteoclast Functions by Fibroblast Growth Factor (FGF)-18 in Comparison with FGF-2 and FGF-10, J. Biol. Chem., 277(9):7493-500 (2002).

Siebuhr, A. S. et al., Serological identification of fast progressors of structural damage with rheumatoid arthritis, Arthritis Research Therapy, 15(4):1-9 (2013).

Siebuhr, A.S. et al., CRP and a Biomarker of Type I Collagen Degradation, C1M Can Differentiate Anti-Inflammatory Treatment Response in Ankylosing Spondylitis, Biomark. Med., 10(2):197-208 (2016).

Siebuhr, A.S. et al., Identification and Characterisation of Osteoarthritis Patients with Inflammation Derived Tissue Turnover, Osteoarthritis Cartilage, 22(1):44-50 (2014).

Sugiyama, S. et al., Procollagen II C propeptide level in the synovial fluid as a predictor of radiographic progression in early knee osteoarthritis, Ann Rheum Dis, 62:27-32 (2003).

Takahashi, K. et al., The effects of hyaluronan on matrix metalloproteinase-3 (MMP-3), interleukin-1β (IL-1β), and tissue inhibitor of metalloproteinase-1 (TIMP-1) gene expression during the development of osteoarthritis, Osteo. Cart., 7:182-190 (1999).

Tokuriki, N and Tawfik, D.S., Stability effects of mutations and protein evolvability, Curr. Opin. Struc. Biol., 19(5):596-604 (2009).

Valdes, A.M. et al., Intercritical Circulating Levels of Neo-Epitopes Reflecting Matrixmetalloprotease-Driven Degradation as Markers of Gout and Frequent Gout Attacks, Rheumatology (Oxford), 55(9):1642-1646 (2016).

Wolfe, F., Determinants of WOMAC Function, Pain and Stiffness Scores: Evidence for the Role of Low Back Pain, Symptom Counts, Fatigue and Depression in Osteoarthritis, Rheumatoid Arthritis and Fibromyalgia, Rheumatology (Oxford), 38(4):355-361 (1999).

Written Opinion for PCT/EP2018/07639, 6 pages (mailed Nov. 6, 2018).

Written Opinion for PCT/EP2018/076395, filed Sep. 28, 2018, 10 pages, (mailed Nov. 6, 2018).

Written Opinion for PCT/EP2019/074003, filed Sep. 9, 2019, 12 pages, (mailed Oct. 11, 2019).

Wu, X. et al., 390 Progression or initiation of radiographic knee osteoarthritis and the interleukin-1 receptor antagonist gene: the Johnston county osteoarthritis project, Osteo. Cart., 18:S171-172 (2010).

INFLAMMATORY BIOMARKERS FOR PREDICTING RESPONSIVENESS TO FGF-18 COMPOUND

CROSS-REFERENCE TO RELATED APPLICATIONS

This application is a continuation of U.S. patent application Ser. No. 16/650,878, filed Mar. 26, 2020, which is a U.S. national stage application of International Patent Application No. PCT/EP2018/076391, filed Sep. 28, 2018, which claims the benefit of European Patent Application No. 17194169.3, filed Sep. 29, 2017, and European Patent Application No. 18169317.7, filed Apr. 25, 2018, the disclosures of which are incorporated herein by reference in their entirety.

SEQUENCE LISTING

The instant application contains a Sequence Listing with eight sequences, which has been submitted electronically through USPTO Patent Center in XML format and is hereby incorporated by reference in its entirety. Said XML copy, created on Sep. 1, 2022, is named 33280-53521.xml and is 11,200 bytes in size.

FIELD OF INVENTION

The present invention relates to biomarkers associated with the clinical response to an FGF-18 compound before or during treatment of a cartilage disorder. It relates more particularly to specific proteins present in the blood, serum, synovial fluid or in the urine, which can be used as biomarkers for the diagnosis, pre-treatment of patients and during therapy of cartilage disorders. The invention further discloses specific proteins that are related to cartilage response to an FGF-18 compound treatment as well as diagnostic tools and kits based on their quantities or expression profile of proteins related to tissue inflammation. Thus, the invention can be used in predicting the response to an FGF-18 compound treatment, before starting the treatment or during the treatment. It could be used for selecting/identifying subjects to be treated according to specific doses and/or dosing regimens by intra-articular administration of an FGF-18 compound. The use of these biomarkers in diagnostics could result in increased benefit and reduced risk-benefit ratio in subjects.

BACKGROUND OF THE INVENTION

Cartilage disorders broadly refer to diseases characterized by degeneration of metabolic abnormalities in the connective tissues which are manifested by pain, stiffness and limitation of motion of the affected body parts. These disorders can be due to pathology or can be the result of trauma or injury. Among others, cartilage disorders include osteoarthritis (OA), cartilage injury (inclusive sports injuries of cartilage and joint, and surgical injuries such as microfracture(s)). Mature cartilage has limited ability to repair itself, notably because mature chondrocytes have little potential for proliferation and due to the absence of blood vessels. In addition, cartilage is not well nutrified and has a low oxygen pressure. Replacement of damaged cartilage, in particular articular cartilage, caused either by injury or disease is a major challenge for physicians, and available surgical treatment procedures are considered not completely predictable and effective for only a limited time. Therefore, the majority of younger subjects either does not seek treatment or are counselled to postpone treatment for as long as possible. When treatment is required, the standard procedure is age dependent and varies between total joint replacement, transplantation of pieces of cartilage or marrow stimulating technique (such as microfracture). Microfracture is a common procedure that involves penetration of the subchondral bone to stimulate cartilage deposition by bone marrow derived stem cells. However, it has been shown that this technique does not repair sufficiently the chondral defect and the new cartilage formed is mainly fibrocartilage, resulting in inadequate or altered function and biomechanics. Indeed, fibrocartilage does not have the same durability and may not adhere correctly to the surrounding hyaline cartilage. For this reason, the newly synthesized fibrocartilage may breakdown more easily (expected time frame: 5-10 years). For subjects with osteoarthritis, non-surgical treatment consists notably of physical therapy, lifestyle modification (e.g. increasing physical activity), supportive devices, oral and injected drugs (e.g. non-steroidal anti-inflammatory drugs), walking aids and medical symptom management. Once these treatments fail, surgery, such as joint replacement, is the main option for the subjects. Tibial or femoral osteotomies (cutting the bone to rebalance joint wear) may reduce symptoms, help to maintain an active lifestyle, and delay the need for total joint replacement. Total joint replacement can provide relief for the symptom of advanced osteoarthritis, but generally requires a change in a subject's lifestyle and/or activity level.

At that time, drug treatments on the market are mainly directed to pain relief. There is not yet commercially available treatment that restores or postpones the cartilage damages (see Lotz, 2010; Karsdal, 2016).

Fibroblast Growth factor 18 (FGF-18) is a member of the FGF family of proteins, closely related to FGF-8 and FGF-17. It has been shown that FGF-18 is a proliferative agent for chondrocytes and osteoblasts (Ellsworth et al., 2002; Shimoaka et al., 2002; Gigout et al., 2017). FGF-18 has been proposed for the treatment of cartilage disorder such as osteoarthritis and cartilage injury either alone (WO2008/023063) or in combination with hyaluronic acid (WO2004/032849).

Sprifermin, which is a truncated form of human FGF-18, is being investigated in clinical trials for treatment of both osteoarthritis and cartilage injury (for more details see for instance NCT01033994, NCT00911469 and NCT01066871). The current dosing regimen for sprifermin is once weekly for 3 weeks (one treatment cycle), the drug being administered via intraarticular injections. This treatment cycle can be repeated. This dosing regimen has been described in WO2008/023063.

At that time, OA and cartilage injury treatments with FGF-18, during clinical trials, are provided to subjects without predictive information on the response (Lohmander et al., 2014; Dahlberg et al., 2016), i.e. without knowledge on whether the treatment will likely be highly effective, moderately effective or show only little or no effect. Currently, numerous treated subject population exhibit an intermediate/high response to treatment according to the WOMAC scores with sprifermin after at least one treatment cycle, however, some others either do not respond to said treatment or respond while presenting higher WOMAC score compared to control.

WO2014/023703 describes genetic markers (combination of SNPs IL-1RN rs9005 and IL-1RN rs315952) that are associated with the quality of the clinical response to treatment of cartilage disorder such as OA, cartilage injury or microfracture(s) with FGF-18. Such markers are useful for identifying, through genetic screening prior to the treatment, subgroups of subjects that are more likely to exhibit a particular response to treatment with FGF-18, such as a very good clinical response to treatment with FGF-18 or on the contrary those for whom the therapy may fail.

Knowledge on the type of clinical response of a subject to treatment can be used to optimize therapy or select therapy, such as selecting treatment with FGF-18 as a first line therapy or adapting the dose and/or dosing regimen. Such information will be clinically useful for the medical management of cartilage disorder, such as of OA and/or cartilage injury, in subjects. For example, if an individual with OA or cartilage injury is known to be at increased risk for not responding to the FGF-18 treatment at a given dose, the physician may exclude said subject from the FGF-18 treatment or change dose and/or dosing regimen. In addition, such predictive information may also be clinically useful to guide decisions on the dosing regimen.

There is a need to identify further biomarkers helping in optimizing therapy or in selecting a therapy, in order to provide a full range of solution for the subject to be treated or for the doctor looking for the best therapy for his patient.

SUMMARY OF THE INVENTION

As described herein, inflammatory biomarkers such as of C1M, C3M and/or CRPM can be used either alone or in combination in the detection, diagnosis and treatment of patients with osteoarthritis or cartilage disorders. The expression levels (or quantity) of at least one of these biomarkers (or combinations thereof) can be used, for instance, to detect patients to be included in specific dosing regimen for certain therapies, such as sprifermin or a fusion protein comprising an FGF-18 moiety.

The present invention is directed to a method of predicting the sensitivity to treatment with an FGF-18 compound in a subject having a cartilage disorder, the method comprising the steps of:

Determining, from a sample, the quantity of at least one of the biomarkers selected from the group consisting of C1M, C3M and/or CRPM;

Predicting from the result of step a) good or low sensitivity of said subject to treatment with an FGF-18 compound.

According to said method, the presence of lower than $30.0\pm2$ SD ng/mL of C1M and/or lower than $12.0\pm2$ SD ng/mL of C3M and/or lower than $10.0\pm2$ SD ng/mL of CRPM is predictive of good response (i.e. response or sensitivity) to treatment with an FGF-18 compound. FGF-18 compound could thus be administered to said subject at the following dosing regimen: at least two treatment cycles of 100 µg of the FGF-18 compound given once per week for 3 consecutive weeks per treatment cycle. On the contrary, the presence of higher than $30.0\pm2$ SD ng/mL of C1M and/or higher than $12.0\pm2$ SD ng/mL of C3M and/or higher than $10.0\pm2$ SD ng/mL of CRPM is predictive of low response (i.e. low sensitivity) to treatment with an FGF-18 compound. FGF-18 compound could thus be administered to said subject preferably at the following dosing regimen: four treatment cycles of 100 µg of FGF-18 compound given once per week for 3 consecutive weeks per treatment cycle.

Also described herein is a method for selecting a subject having a cartilage disorder for inclusion in or exclusion from a specific dosing regimen when said subject is to be treated with an FGF-18 compound, based on the likelihood of their sensitivity to said treatment, comprising the steps of:

a) Determining, from a sample, the quantity of at least one of the biomarkers selected from the group consisting of C1M, C3M and/or CRPM; wherein the quantity of at least one of these proteins is predictive about the subject's risk of having good-sensitivity or low-sensitivity to said treatment, and b) Selecting the appropriate dosing regimen according to the subject's risk of having good-sensitivity or low-sensitivity to said treatment.

According to said method, the subject presenting higher than $30.0\pm2$ SD ng/mL of C1M and/or higher than $12.0\pm2$ SD ng/mL of C3M and/or higher than $10.0\pm2$ SD ng/mL of CRPM will preferably be excluded (i.e. they will not be selected) from the treatment with FGF-18 compound given at the following dosing regimen: two treatment cycles of 100 µg of FGF-18 compound given once per week for 3 consecutive weeks per treatment cycle. To the contrary, the subject presenting lower than $30.0\pm2$ SD ng/mL of C1M and/or lower than $12.0\pm2$ SD ng/mL of C3M and/or lower than $10.0\pm2$ SD ng/mL of will be included (i.e. they will be selected) for the treatment with FGF-18 compound given at the following dosing regimen: at least two treatment cycles of 100 µg of FGF-18 compound given once per week for 3 consecutive weeks per treatment cycle.

Also described herein is a kit comprising means for performing the method according to the invention as a whole.

Also encompassed is an FGF-18 compound for use in the treatment of a subject having a cartilage disorder, characterized in that:

If the subject has lower than $30.0\pm2$ SD ng/mL of C1M and/or lower than $12.0\pm2$ SD ng/mL of C3M and/or lower than $10.0\pm2$ SD 10 ng/mL of CRPM he can receive a treatment with an FGF-18 compound given at the following dosing regimen at least two treatment cycles of 100 µg of FGF-18 compound given once per week for 3 consecutive weeks per treatment cycle and, If the subject has higher than $30.0\pm2$ SD ng/mL of C1M and/or higher than $12.0\pm2$ SD ng/mL of C3M and/or higher than $10.0\pm2$ SD ng/mL of CRPM he can receive a treatment with an FGF-18 compound given at the following dosing regimen: four treatment cycles of 100 µg of FGF-18 compound given once per week for 3 consecutive weeks per treatment cycle.

Also described is a method for treating a subject having a cartilage disorder, comprising the following steps:

a) Determining, from a sample, the quantity of at least one of the biomarkers selected from the group consisting of C1M, C3M and/or CRPM, wherein said quantities are predictive about the subject's risk of having good or low sensitivity to a treatment with said FGF-18 compound, b) Selecting the appropriate dosing regimen according to the subject's risk of having good-sensitivity or low-sensitivity to said treatment, and c) Administering intraarticularly an FGF-18 compound according to the dosing regimen selected in step b).

According to said method, the presence of lower than $30.0\pm2$ SD ng/mL of C1M and/or lower than $12.0\pm2$ SD ng/mL of C3M and/or lower than $10.0\pm2$ SD ng/mL of CRPM is predictive of good response (i.e. response or sensitivity) to treatment with an FGF-18 compound in a dose-dependent way. FGF-18 compound could thus be administered to said subject at the following dosing regimen: at least two treatment cycles of 100 µg of FGF-18 compound given once per week for 3 consecutive weeks per treatment cycle. On the contrary, the presence of higher than $30.0\pm2$ SD ng/mL of C1M and/or higher than $12.0\pm2$ SD ng/mL of C3M and/or higher than 10.0±2 SD ng/mL of CRPM is predictive of low response (i.e. low sensitivity) to treatment with an FGF-18 compound. FGF-18 compound could thus be administered to said subject preferably at the following dosing regimen: four treatment cycles of 100 μg of FGF-18 compound given once per week for 3 consecutive weeks per treatment cycle.

In particular embodiments of the present invention as a whole, i.e. in any of the methods or uses mentioned herein, the FGF-18 compound to be used as a treatment is sprifermin or a fusion protein comprising an FGF-18 moiety and the subject has a cartilage disorder selected from the group consisting of osteoarthritis, cartilage injury, fractures affecting joint cartilage or surgical procedures with impact on joint cartilage (e.g. Microfracture).

It is to be understood that in any of the methods or uses mentioned herein, before determining the quantity of at least one of the proteins, it is needed to obtain a sample (or a test sample) of said subject, via for instance blood, serum, synovial fluid or urine collecting. Further, it is also to be understood that any of the methods or uses mentioned herein are performed in vitro, and not on the animal or human body.

Definitions

The term "FGF-18 compound" or "FGF-18", as used herein, is intended to be a protein maintaining at least one biological activity of the human FGF-18 protein. FGF-18 may be native, in its mature form, or a truncated form thereof. Biological activities of the human FGF-18 protein include notably the increase in osteoblastic activity (see WO98/16644) or in cartilage formation (see WO2008/023063). Native, or wild-type, human FGF-18 is a protein mostly produced during skeletal development and is involved in bone and cartilage formation (See Haque et al., 2007). Human FGF-18 was first designated zFGF-5 and is fully described in WO98/16644. SEQ ID NO:1 corresponds to the amino acid sequence of the native human FGF-18, with a signal peptide consisting of amino acid residues 1(Met) to 27(Ala). The mature form of human FGF-18 corresponds to the amino acid sequence from residue 28(Glu) to residue 207(Ala) of SEQ ID NO: 1 (180 amino acids).

The FGF-18 compound, in the present invention, may be produced by recombinant methods, such as taught by the application WO2006/063362. Depending on the expression systems and conditions, FGF-18 in the present invention is expressed in a recombinant host cell with a starting Methionine (Met) residue or with a signal sequence for secretion. When expressed in prokaryotic host, such as in *E. coli*, FGF-18 contains an additional Met residue in N-terminal of its sequence. For instance, the amino acid sequence of human FGF-18, when expressed in *E. coli*, starts with a Met residue in N-term (position 1) followed by residues 28 (Glu) to residue 207 (Ala) of SEQ ID NO: 1.

The term "FGF-18 compound" also includes variants or mutants of the native, mature form, or truncated forms of FGF-18, as well as fusion proteins comprising a (biologically) active FGF-18 moiety coupled to a heterologous protein or a chemical compound (such as those disclosed in EP17192467.3 patent family). In such fusion proteins, the FGF-18 moiety can be the native, mature form, or truncated forms of the FGF-18 protein or variants or mutants thereof.

The term "truncated form" of FGF-18, as used herein, refers to a protein which comprises or consists of residues 28(Glu) to 196(Lys) of SEQ ID NO: 1. Preferably, the truncated form of FGF-18 protein is the polypeptide designated "trFGF-18" (170 amino acids), which starts with a Met residue (in N-terminal) followed by amino acid residues 28 (Glu) –196 (Lys) of the wild-type human FGF-18. The amino acid sequence of trFGF-18 is shown in SEQ ID NO:2 (amino acid residues 2 to 170 of SEQ ID NO:2 correspond to amino acid residues 28 to 196 of SEQ ID NO:1). trFGF-18 is a recombinant truncated form of human FGF-18, produced in *E. coli* (see WO2006/063362). The International Non-proprietary Name (INN) for this particular form of FGF-18 is sprifermin. Sprifermin has been shown to display similar activities as the mature human FGF-18, e.g. it increases chondrocyte proliferation and cartilage deposition leading to repair and reconstruction for a variety of cartilaginous tissues (see WO2008/023063).

The term "marker" or "biomarker" are used interchangeably. In the context of the present invention they are proteins. A "prognostic biomarker" is informative about the subject condition, including and not limited to disease evolution, disease severity or disease outcome, regardless of any therapy. A "predictive biomarker" is informative about the effect of a received therapy, including, but not limited to efficacy and safety outcome. The prognostic and predictive definitions are not mutually exclusive thus a biomarker can be both prognostic and predictive. The quantity of biomarker or the expression level of biomarker is herein expressed as ng, μg, mg or g of a given protein. Said quantity or level can be expressed as absolute value (e.g. 10 ng or 2 μg) or as concentration (e.g. 10 ng/mL or 2 μg/mL). In relation to the biomarkers, the term "quantity" or "expression level" can be used interchangeably.

The term "inflammatory biomarker" refers to biomarkers such as CRPM, C1M, and C3M.

The term "CRPM" refer to C-reactive protein degraded by metalloproteinase (MMP) enzymatic activity generating a neo-epitope with sequence KAFVFP (SEQ ID NO: 6) as specific epitope recognised by the assay: CRPM is a novel tissue-related measure of C-reactive protein (CRP). The difference between standard CRP and CRPM is that CRPM measure a degradation product of CRP; whereas CRP is an acute reactant released from the liver, CRPM is a product released after CRP has exerted its effect on the tissue. Thus CRPM is a measure of tissue inflammation. CRPM has been measured in different OA and RA studies and have shown to be associated disease activity and pain measures. More CRPM have shown to be prognostic for OA incidence (see e.g. Siebuhr et al. 2014 or Saberi Hosnijeh et al., 2016)

The term "C1M" refers to Collagen type I degraded by MMP enzymatic activity generating a neo-epitope with sequence KDGVRG (SEQ ID NO: 7) as specific epitope recognised by C1M assay. C1M assay measures type I collagen degradation mediated by MMP. This reflects connective tissue degradation. A significant association between baseline C1M and change to joint space narrowing was observed in RA. In addition, C1M is significantly associated with disease activity (e.g. DAS) modulated by anti-inflammatories such as tocilizumab and infliximab in RA and SpA (see e.g. Siebuhr et al., 2013 or Siebuhr et al., 2016).

The term "C3M" refers to Collagen type 3 degraded by MMP, generating a neo-epitope with sequence KNGETG (SEQ ID NO: 8) as specific epitope recognised by C3M assay: C3M measures type III collagen degradation mediated by MMP. This reflects connective tissue degradation and seems to especially associate with joint inflammation. It is highly associated with inflammation, tissue health, disease activity and response to treatment. A significant association between baseline C3M to disease activity and it is predictive of treatment response in RA. Furthermore, there is a significant association of C3M with occurrence of flares in gout and are associated with an inflammatory phenotype in OA. In addition, C3M is modulated by anti-inflammatories such as tocilizumab and infliximab in RA and SpA. (See e.g. Valdes et al., 2016 or Maijer et al. 2016).

"Cartilage disorder", as used herein, encompasses disorders resulting from damages due to injury, such as traumatic injury, chondropathy or arthritis. Examples of cartilage disorders that may be treated by the administration of the FGF-18 formulation described herein include but are not restricted to arthritis, such as osteoarthritis, cartilage injury, fractures affecting joint cartilage or surgical procedures with impact on joint cartilage (e.g. Microfracture). Degenerative diseases/disorders of the cartilage or of the joint, such as chondrocalcinosis, polychondritis, relapsing polychondritis, ankylosing spondylitis or costochondritis are also encompassed by this wording. The International Cartilage Repair Society has proposed an arthroscopic grading system to assess the severity of the cartilage defect: grade 0: (normal) healthy cartilage, grade 1: the cartilage has a soft spot or blisters, grade 2: minor tears visible in the cartilage, grade 3: lesions have deep crevices (more than 50% of cartilage layer) and grade 4: the cartilage tear exposes the underlying (subchondral) bone (see for instance page 13 of cartilage.org/files/contentmanagement/ICRS evaluation.pdf).

The term "SD" means standard deviation and is linked to the usual deviations of any validation assays/systems.

The term "Osteoarthritis" is used to intend the most common form of arthritis. The term "osteoarthritis" encompasses both primary osteoarthritis and secondary osteoarthritis (see for instance The Merck Manual, 17th edition, page 449). The most common way of classifying/grading osteoarthritis is the use of the Kellgren-Lawrence radiographic grading scale (see table below). Osteoarthritis may be caused by the breakdown of cartilage. Bits of cartilage may break off and cause pain and swelling in the joint between bones. Over time, the cartilage may wear away entirely, and the bones will rub together. Osteoarthritis can affect any joint but usually concerns hands and weight-bearing joints such as hips, knees, feet, and spine. In a preferred example, the osteoarthritis may be knee osteoarthritis or hip osteoarthritis. Osteoarthritis is one of the preferred cartilage disorders that can be treated by administering the FGF-18 compounds according to the present invention.

Kellgren-Lawrence Radiographic Grading Scale of Osteoarthritis is described as follow:

| Grade of Osteoarthritis | Description |
| --- | --- |
| 0-None | No radiographic findings of osteoarthritis |
| 1-Doubtful | Doubtful narrowing of joint space and possible osteophytic lipping |
| 2-Minimal | Definite osteophytes, definite narrowing of joint space |
| 3-Moderate | Moderate multiple osteophytes, definite narrowing of joints space, some sclerosis and possible deformity of bone contour |
| 4-Severe | Large osteophytes, marked narrowing of joint space, severe sclerosis and definite deformity of bone contour |

Grades 1 and 2 can be considered as less severe forms of the disease, whereas grades 3 and 4 can be considered as more severe forms of the disease.

The term "cartilage injury" as used herein is a cartilage disorder or cartilage damage resulting notably from a trauma. Cartilage injuries can occur notably after traumatic mechanical destruction, notably further to an accident or surgery (for instance microfracture surgery). This term "cartilage injury" also includes chondral or osteochondral fracture, damage to meniscus, and the term microfracture. Also considered within this definition is sport-related injury or sport-related wear of tissues of the joint.

"WOMAC total scores" or "WOMAC scores" ("WOMAC" for "Western Ontario and McMaster Universities Osteoarthritis Index") measure pain (WOMAC pain score), function (WOMAC function score) and stiffness (WOMAC stiffness score). When applied to assessing of pain and dysfunction associated with cartilage injury, it consists of a questionary containing 24 items divided into 3 subscales (5 items for Pain, 2 items for Stiffness and 17 items for Physical Function)(see Bellamy et al., 1988; Wolfe, 1999). It is a well-known instrument, widely used notably in assessment of the OA severity.

In order to evaluate cartilage repair, cartilage volume measurements were performed through magnetic resonance imaging (MRI) measurements, including but not exclusively: Lateral volume of cartilage (also referred as LFTC), Medial volume of cartilage (also referred as MFTC), Total volume of cartilage (also referred as LFTC+MFTC), and new total average cartilage thickness.

The term "baseline" means before treatment (i.e. at study entry). It refers notably to clinical variables, such as, but not limited to, the cartilage volume and WOMAC total score of one given subject at study entry (i.e. before treatment with FGF-18 compound or placebo).

The term "subject" or "patient" refers to both human and non-human animals. The term non human comprises mammals such as rodents (including mice), rabbits, cats, dogs, horses, cows, sheep, or primates.

"Sensitives" are subjects that exhibit a response to treatment of a cartilage disorder with an FGF-18 compound. Preferably, sensitive subjects (or subjects showing sensitivity to treatment) exhibit notably a higher increase in total cartilage volume than placebo treated subjects, i.e. they show cartilage repair. In addition, sensitive subjects exhibit at least similar improvement in WOMAC total scores than placebos. The terms "good-responders" (or good sensitive), and "low-responders" (including "Low-sensitive") refer to the different groups of subjects depending notably on the increase of the cartilage volume following specific dosing regimen in the frame of a FGF-18 compound treatment. A good responder displays a positive response (i.e. cartilage repair) to treatment with an FGF-18 compound whatever the dosing regimen, whereas low responder display a response only to a specific dosing regimen when treated with an FGF-18 compound. Both groups of responders have similar improvement in WOMAC total score than placebos, should they be treated according to specific dosing regimen. The good responders can also be simply called responders or sensitive (patients). A good response can also be called response.

The proposed criteria for sensitivity are the following:
Positive cartilage increase compared to baseline,
Cartilage increase change significantly higher than change in placebo (e.g. as tested with a linear model adjusting for BMI, KL grade, sex and age and with alpha=5%), WOMAC score improvement, i.e. diminution, (e.g. more than 5 points reduction) compared to baseline,
WOMAC score change not significantly higher than change in placebo (e.g. as tested with a linear model adjusting for BMI, KL grade, sex and age and with alpha=5%)

The "response", or "sensitivity" to an FGF-18 compound treatment is to be understood as 1 year or 2 years after the first injection and measured as 1) increase of cartilage volume and/or cartilage thickness, measured owing to MRI or X-Ray for instance, 2) decrease of WOMAC total scores, or 3) changes in WOMAC total scores not significantly higher than those from placebos (refer also to the definition of "sensitive").

As used in the present invention, the term "MAD" means Multiple Ascending Dose. When this acronym is followed by a figure, the figure corresponds to the dose at which FGF-18 compound has been injected during treatment. For instance MAD100 refers to a treatment during which a subject received 100 mcg of FGF-18 compound per injection. The abbreviation "PL" (and "MADPL") refers to placebo.

The term "storage device", as used herein, is intended to include any suitable computing or processing apparatus or other device configured or adapted for storing data or information. Examples of electronic apparatus suitable for use with the present invention include stand-alone computing apparatus, data telecommunications networks, including local area networks (LAN), wide area networks (WAN), Internet, Intranet, and Extranet, and local and distributed computer processing systems. Storage devices also include, but are not limited to: magnetic storage media, such as floppy discs, hard disc storage media, magnetic tape, optical storage media such as CD-ROM, DVD, electronic storage media such as RAM, ROM, EPROM, EEPROM and the like, general hard disks and hybrids of these categories such as magnetic/optical storage media.

As used herein, the term "stored" refers to a process for encoding information on the storage device. Those skilled in the art can readily adopt any of the presently known methods for recording information on known media to generate manufactures comprising expression level information.

DETAILED DESCRIPTION OF THE INVENTION

There is a need to predict the clinical efficacy (notably with regards to delaying cartilage thinning and/or cartilage repair) of an FGF-18 compound treatment for the treatment of subjects having a cartilage disorder, such as osteoarthritis, cartilage injury, fractures affecting joint cartilage or surgical procedures with impact on joint cartilage (e.g. Microfracture). To optimize the treatment of said subjects, it is important to identify biomarkers that could be used as predictors of the response of a given subject to a specific dosage regimen in the frame of a FGF-18 compound treatment, notably with regard to cartilage repair. Such predictive biomarkers may be used to identify groups having risks of being low-sensitives to a given dose regimen. For instance, if one subject having osteoarthritis is known to be at risk for having a low-response (or for being low-sensitive) to the FGF-18 compound treatment, the physician may decide to propose a four cycle-treatment with a FGF-18 compound, such as sprifermin, to said subject. Such predictive information may be clinically useful to guide medical decisions, notably on the dosing regimen to be applied to one patient.

The surprising finding of the present invention is based on a study aimed at identifying potential biomarkers associated with FGF-18 compound administration. The biomarkers used in this study were composed of numerous protein markers. The association between protein markers and clinical response variables was assessed. The rationale behind this type of analysis was to identify protein(s) useful as biomarker(s) that could be predictive of the clinical outcome (notably with regard to cartilage repair), for a subject to be treated with an FGF-18 compound such as sprifermin or a fusion protein comprising an FGF-18 moiety. The proteins could be used to stratify and target specific subject populations.

The inventors have surprisingly found an association with certain proteins and outcome (e.g. cartilage repair). Of special interest are the proteins C1M, C3M and/or CRPM. It is noted that although only C1M, C3M and/or CRPM are specifically described herein, other inflammatory biomarker such as high-sensitivity C-reactive protein (hs-CRP) could be used. Based on the teaching of the present invention, it would then be routine matter for the skilled person to find the thresholds for each of these biomarkers.

These proteins have been described in the literature, as being possibly related to inflammation in arthritis. For instance, C1M, C3M and/or CRPM could be considered as inflammatory biomarkers, specific for tissue inflammation. The results presented herein show that high levels of tissue inflammation abolish the therapeutic effect of an FGF-18 compound (such as sprifermin), especially at lower doses/dosing regimens. This abolishing effect can be surprisingly counteract with an FGF-18 compound (such as sprifermin) administered at a particular dosing regimen.

It has also been surprisingly found by the present inventors that when the quantity of inflammatory biomarkers such as C1M, C3M and/or CRPM is/are decreased, this is associated with a better response to treatment with a FGF-18 compound, such as sprifermin or a fusion protein comprising an FGF-18 moiety, whatever the dosing regimen in subjects afflicted with cartilage injury. These subjects are called good-sensitives or good-responders. To the opposite, it has also surprisingly been found by the present inventors that when the quantity of C1M, C3M and/or CRPM is/are increased, this is associated with a lower response to treatment with a FGF-18 compound (i.e. low-sensitivity to treatment with a FGF-18 compound), such as sprifermin or a fusion protein comprising an FGF-18 moiety, in subjects afflicted with cartilage disorder, except at a specific dosing regimen comprising four cycles of treatment. These subjects are called low-sensitives or low-responders. It was further surprisingly been found that each one of these biomarkers can be used alone to provide an efficient prediction of the response to FGF-18.

Therefore, it is a finding of the present invention that the biomarkers C1M, C3M and/or CRPM can be used either alone or in combination as predictive biomarkers of responsiveness of one subject to specific dosing regimen in the frame of a FGF-18 compound treatment, such as sprifermin or a fusion protein comprising an FGF-18 moiety. Preferably, the subject has a cartilage disorder, such as osteoarthritis, cartilage injury, fractures affecting joint cartilage or surgical procedures with impact on joint cartilage (e.g. Microfracture). In a particular embodiment, the subject will be predicted to be low-sensitive to FGF-18 compound treatment if the quantity of C1M is higher than 30.0±2 SD ng/mL and/or if the quantity of C3M is higher than 12.0±2 SD ng/mL and/or if the quantity of CRPM is higher than 10.0±2 SD ng/mL. On the contrary, the subject will be predicted to be sensitive (or responder or good responder) to FGF-18 compound treatment if the quantity of C1M is lower than 30.0±2 SD ng/mL and/or the quantity of C3M is lower than 12.0±2 SD ng/mL and/or the quantity of CRPM is lower than 10.0±2 SD ng/mL.

The present invention is therefore directed to a method of predicting the sensitivity to treatment with an FGF-18 compound in a subject having a cartilage disorder, the method comprising the steps of:
  Determining, from a biological sample of said subject, the quantity of at least one of the biomarkers selected from the group consisting of C1M, C3M and/or CRPM; and
  Predicting from the result of step a) good or low sensitivity of said subject to treatment with an FGF-18 compound.

Before determining the quantity of at least one of the biomarkers, it is needed to obtain a sample (or biological sample or test sample) of said subject, for instance by blood, serum, synovial fluid or urine collecting. Thus, the present invention is directed to a method of predicting the sensitivity to treatment with an FGF-18 compound in a subject having a cartilage disorder, the method comprising the steps of:
  Obtaining a sample from said subject;
  Determining, from a sample, the quantity of at least one of the biomarkers selected from the group consisting of C1M, C3M and/or CRPM; and
  Predicting from the result of step a) good or low sensitivity of said subject to treatment with an FGF-18 compound According to said method, the presence of lower than 30.0±2 SD ng/mL of C1M and/or lower than 12.0±2 SD ng/mL of C3M and/or lower than 10.0±2 SD ng/mL of CRPM is predictive of good response (or response or sensitivity) to treatment with an FGF-18 compound. FGF-18 compound could thus be administered to said subject at the following dosing regimen at least two treatment cycles of 100 µg of FGF-18 compound given once per week for 3 consecutive weeks per treatment cycle. On the contrary, the presence of higher than 30.0±2 SD ng/mL of C1M and/or higher than 12.0±2 SD ng/mL of C3M and/or higher than 10.0±2 SD ng/mL of CRPM is predictive of low response (i.e. low sensitivity) to treatment with an FGF-18 compound. FGF-18 compound could thus be administered to said subject preferably at the following dosing regimen: four treatment cycles of 100 µg of FGF-18 compound given once per week for 3 consecutive weeks per treatment cycle.

The present application also encompasses a method for selecting a subject having a cartilage disorder for inclusion in or exclusion from a dosing regimen when said subject is to be treated with an FGF-18 compound, based on the likelihood of their sensitivity to said treatment, comprising the steps of:
  Determining, from a sample, the quantity of at least one of the biomarkers selected from the group consisting of C1M, C3M and/or CRPM; wherein the quantity of at least one of these proteins is predictive about the subject's risk of having good-sensitivity or low-sensitivity to said treatment, and
  Selecting the appropriate dosing regimen according to the subject's risk of having good-sensitivity or low-sensitivity to said treatment.

Before determining the quantity of at least one of the proteins, in the above disclosed assays, it is needed to obtain a sample (or test sample or biological sample) of said subject, for instance by blood, serum, synovial fluid or urine collecting. Thus, the present invention is directed to a method for selecting a subject having a cartilage disorder for inclusion in or exclusion from dosing regimen when said subject is to be treated with an FGF-18 compound, based on the likelihood of their sensitivity to said treatment, comprising the steps of:
  Obtaining a biological sample from said subject,
  Determining, from a sample, the quantity of at least one of the biomarkers selected from the group consisting of C1M, C3M and/or CRPM; wherein the quantity of at least one of these proteins is predictive about the subject's risk of having good-sensitivity or low-sensitivity to said treatment, and
  Selecting the appropriate dosing regimen according to the subject's risk of having good-sensitivity or low-sensitivity to said treatment.

According to said method, the subject presenting higher than 30.0±2 SD ng/mL of C1M and/or higher than 12.0±2 SD ng/mL of C3M and/or higher than 10.0±2 SD ng/mL of CRPM will preferably be excluded (i.e. they will not be selected) from the treatment with FGF-18 compound given at the following dosing regimen: two treatment cycles of 100 µg of FGF-18 compound given once per week for 3 consecutive weeks per treatment cycle. Sais subject would preferably be proposed the following dosing regimen: four treatment cycles of 100 µg/mL of FGF-18 compound (such as sprifermin) given once per week for 3 consecutive weeks per treatment cycle. To the contrary, the subject presenting lower than 30.0±2 SD ng/mL of C1M and/or lower than 12.0±2 SD ng/mL of C3M and/or lower than 10.0±2 SD ng/mL of will be included (i.e. they will be selected) for the treatment with FGF-18 compound given at the following dosing regimen: at least two treatment cycles of 100 µg of FGF-18 compound given once per week for 3 consecutive weeks per treatment cycle.

The method for selecting a human subject for a clinical trial for testing FGF-18 compound, may alternatively comprises the steps of:
  a) assaying a biological sample from said human subject diagnosed with a cartilage disorder for the quantity of at least one of C1M, C3M and/or CRPM,
  b) determining the quantity of the at least one of C1M, C3M and/or CRPM; and
  c) selecting:
    i. for the clinical trial at the following dosing regimens: at least two treatment cycles of 100 µg of FGF-18 compound given once per week for 3 consecutive weeks per treatment cycle the human subject who presents lower than 30.0±2 SD ng/mL of C1M and/or lower than 12.0±2 SD ng/mL of C3M and/or lower than 10.0±2 SD ng/mL of CRPM, or ii. for the clinical trial at the following dosing regimens: four treatment cycles of 100 µg of FGF-18 compound given once per week for 3 consecutive weeks per treatment cycle the human subject who presents higher than 30.0±2 SD ng/mL of C1M and/or higher than 12.0±2 SD ng/mL of C3M and/or higher than 10.0±2 SD ng/mL of CRPM.

The present invention also describes a method of excluding a human subject from a clinical trial testing FGF-18 compound at the following dosing regimens: two treatment cycles of 100 µg of FGF-18 compound given once per week for 3 consecutive weeks per treatment cycle, the method comprising the steps of: (a) assaying a biological sample from said human subject diagnosed with a cartilage disorder for the quantity of at least one of C1M, C3M and/or CRPM; (b) determining from said assay the likelihood of the subject of low sensitive to said treatment and (c) excluding for the clinical trial the human subject who presents higher than 30.0±2 SD ng/mL of C1M and/or higher than 12.0±2 SD ng/mL of C3M and/or higher than 10.0±2 SD ng/mL of CRPM.

The quantity (or the expression level) of one or more biomarkers in a sample can be compared, if needed, to a reference quantity (or reference expression level) from a reference sample. Said reference level can be obtained from a healthy subject, or from the very same patient to be diagnosed or treated prior to or during said treatment.

FGF-18 compound is to be usually administered intraarticularly at a dose of 100 mcg per injection, once weekly for 3 weeks per treatment cycle. FGF-18 compound is to be usually administered for at least one treatment cycle of treatment. Preferably, said treatment cycle is repeated at least once, for instance 6 months (or about 26 weeks) after the start of the first treatment cycle. Up to four treatment cycles within 2 years have shown promising results (see FIG. 1).

The present invention further encompasses an FGF-18 compound for use in the treatment of a subject having a cartilage disorder, wherein the FGF-18 compound is administered at the following dosing regimen: at least two treatment cycles of 100 µg of FGF-18 compound given once per week for 3 consecutive weeks per treatment cycle, characterized in that the subject has lower than 30.0±2 SD ng/mL of C1M and/or lower than 12.0±2 SD ng/mL of C3M and/or lower than 10.0±2 SD ng/mL of CRPM. A subject who does not meet these criteria is preferably administered FGF-18 compound according to the following dose regime: four treatment cycles of 100 µg of FGF-18 compound given once per week for 3 consecutive weeks per treatment cycle.

The present invention also relates to an assay to determine sensitivity to an FGF-18 compound treatment or to determine a treatment regimen with an FGF-18 compound, the assay comprising: (a) subjecting a test sample from a human subject, diagnosed as having a cartilage disorder, to at least one assay that determines the quantity of at least one of C1M, C3M and/or CRPM, (b) determining the quantity of at least one of C1M, C3M and/or CRPM and (c) determining from the result of step b) good-sensitivity or low-sensitivity of said subject to treatment with an FGF-18 compound. According to said assay, the presence of higher than 30.0±2 SD ng/mL of C1M and/or higher than 12.0±2 SD ng/mL of C3M and/or higher than 10.0±2 SD ng/mL of CRPM is predictive of low-sensitivity to treatment with an FGF-18 compound, requiring preferably a treatment comprising four-cycles of FGF-18 treatment. On the contrary, the presence of lower than 30.0±2 SD ng/mL of C1M and/or lower than 12.0±2 SD ng/mL of C3M and/or lower than 10.0±2 SD ng/mL of CRPM is predictive of good sensitivity (or of sensitivity).

Before determining the quantity of at least one of the biomarkers, in the above disclosed assays, it is needed to obtain a biomarker (or test) sample of said subject, for instance by blood, serum, synovial fluid or urine collecting.

The present invention is also directed to an assay for selecting a treatment regimen for a human subject with a cartilage disorder, the assay comprising: (a) subjecting a test sample from a human subject, diagnosed as having a cartilage disorder, to at least one assay that determines the quantity of at least one of C1M, C3M and/or CRPM, (b) determining the likelihood that said subject is intermediate-sensitive or a high-sensitive to FGF-18 treatment, and (c) determining from the result of step b) the appropriate treatment regimen for said subject. Once the assay is performed, said subject can be selected for and treated with an appropriate dosing regimen consisting of 1) at least two treatment cycles of 100 µg of FGF-18 compound given once per week for 3 consecutive weeks per treatment cycle when the subject has lower than 30.0±2 SD ng/mL of C1M and/or lower than 12.0±2 SD ng/mL of C3M and/or lower than 10.0±2 SD ng/mL of CRPM based on the recognition that said quantities are associated with a response to said compound (i.e. the subject is intermediate-sensitive or a high-sensitive to FGF-18 treatment), and excluding the subject from treatment with an FGF-18 compound according to said dosing regimen when the subject has higher than 30.0±2 SD ng/mL of C1M and/or higher than 11.7 ng/mL of C3M and/or higher than 10 ng/mL of CRPM based on the recognition that said quantities are associated with inadequate response to treatment with said compound.

Also described is a method for treating a subject having a cartilage disorder, comprising the following steps:
Determining, from a sample, the quantity of at least one of the biomarkers selected from the group consisting of C1M, C3M and/or CRPM, wherein said quantities are predictive about the subject's risk of having good or low sensitivity to a treatment with said FGF-18 compound,
Selecting the appropriate dosing regimen according to the subject's risk of having good-sensitivity or low-sensitivity to said treatment, and
Administering intraarticularly an FGF-18 compound according to the dosing regimen selected in step b).

Further discloses is a method for treating a human subject with a cartilage disorder, comprising the steps of: (a) assaying a biological sample of a subject, who is diagnosed as having the cartilage disorder for the quantity of at least one of the biomarkers selected from the group consisting of C1M, C3M and/or CRPM; and (b) administering a treatment regimen consisting of at least two treatment cycles of 100 µg of FGF-18 compound given once per week for 3 consecutive weeks per treatment cycle when the subject has lower than 30.0±2 SD ng/mL of C1M and/or lower than 12.0±2 SD ng/mL of C3M and/or lower than 10.0±2 SD ng/mL of CRPM.

In the context of the present invention as a whole, C1M, C3M and/or CRPM have been shown to be useful predictive biomarkers of the response to an FGF-18 compound. As such they are considered as predictive biomarkers.

In the context of the present invention as a whole, the assays or other determination of the quantity of at least one of the biomarkers of the invention can be performed before treatment or during treatment. Indeed, also during treatment the dosing regimen may have to be adapted to the new biomarkers situation.

In the context of the invention as a whole, for the patients being in the range of 30±2 SD ng/mL of C1M, 12.0±2 SD ng/mL of C3M or 10.0±2 SD ng/mL of CRPM, it is advisable to complete the diagnostic or the biomarker testing with another inflammatory biomarker. For instance, should the level of C1M be in the range of 30±2 SD ng/mL, then the level(s) of C3M and/or CRPM could be considered. In the rare case where the patient will present ranges of 30±2 SD ng/mL of C1M and 12.0±2 SD ng/mL of C3M and 10.0±2 SD ng/mL of CRPM, then it will be advisable to complete the diagnostic or the biomarker testing with another kind of biomarkers such as a metabolic biomarker or SNP biomarkers such as those disclosed in WO2014023703.

In the context of the present invention as a whole, a dosing regimen consisting of at least two treatment cycles of 100 μg of FGF-18 compound given once per week for 3 consecutive weeks per treatment cycle means any one of: 1) two treatment cycles of 100 μg of FGF-18 compound given once per week for 3 consecutive weeks per treatment cycle, 2) three treatment cycles of 100 μg of FGF-18 compound given once per week for 3 consecutive weeks per treatment cycle, or 3) four treatment cycles of 100 μg of FGF-18 compound given once per week for 3 consecutive weeks per treatment cycle.

In another embodiments of the invention, also provided are systems (and computer readable media for causing computer systems) for obtaining data. Said data can be used notably for assessing suitability of a treatment with FGF-compound in a subject, or monitoring FGF-18 compound treatment efficacy for a given subject or simply monitor disease progression. Said systems can be used during clinical trials, when a treatment with FGF-18 compound has to be envisaged or when a treatment with said compound is already ongoing.

Therefore, in an embodiment of the present invention is included a computer system for obtaining data from at least one test sample obtained from at least one subject with a cartilage disorder, the system comprising: (a) at least one determination module configured to receive said at least one test sample and perform at least one analysis on said at least one test sample to determine the quantity of at least one of the biomarkers according to the invention; (b) at least one storage device configured to store data output from said determination module; and (c) at least one display module for displaying a content based in part on the data output from said determination module, wherein the content comprises a signal indicative of the presence of at least one of these conditions, and optionally the absence of any one of these conditions.

The computer readable medium can have computer readable instructions recorded thereon to define software modules for implementing a method on a computer. In such a case, said computer readable storage medium may comprise: (a) instructions for comparing the data stored on a storage device with reference data to provide a comparison result, wherein the comparison is based on the quantity of at least one of the biomarkers according to the invention; and (b) instructions for displaying a content based in part on the data output from said determination module, wherein the content comprises a signal indicative of the presence of at least one of the conditions, and optionally the absence of one or more of the conditions.

The computer readable storage media can be any available tangible media that can be accessed by a computer. Computer readable storage media includes volatile and 19on-volatile, removable and non-removable tangible media implemented in any method or technology for storage of information such as computer readable instructions, data structures, program modules or other data. Computer readable storage media includes, but is not limited to, RAM (random access memory), ROM (read only memory), EPROM (erasable programmable read only memory), EEPROM (electrically erasable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and non-volatile memory, and any other tangible medium which can be used to store the desired information and which can accessed by a computer including and any suitable combination of the foregoing.

Computer-readable data embodied on one or more computer-readable media may define instructions, for example, as part of one or more programs that, as a result of being executed by a computer, instruct the computer to perform one or more of the functions described herein, and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable media on which such instructions are embodied may reside on one or more of the components of either of a system, or a computer readable storage medium described herein, may be distributed across one or more of such components.

The computer-readable media may be transportable such that the instructions stored thereon can be loaded onto any computer resource to implement the aspects of the present invention discussed herein.

The information determined in the determination module can be read by the storage device. The storage device is adapted or configured for having recorded thereon expression level or protein level information. Such information may be provided in digital form that can be transmitted and read electronically, e.g., via the Internet, on diskette, via USB (universal serial bus) or via any other suitable mode of communication.

In the context of the present invention as a whole, e.g. . . . in the context of any one of the methods, uses, assays or kits according to the present invention, the preferred FGF-18 compound is a truncated FGF-18, such as sprifermin, or a fusion protein comprising an FGF-18 moiety, and the preferred cartilage disorder is selected from the group consisting of osteoarthritis, cartilage injury, fractures affecting joint cartilage or surgical procedures with impact on joint cartilage, such as microfracture.

It is to be understood that in the context of the present invention as a whole, e.g. of any one of the methods, uses, assays, computer system or kits according to the present invention, before determining the quantity of at least one of the biomarkers of the invention (i.e. C1M, C3M and/or CRPM), it is needed to obtain a sample (or biological sample or a test sample) of one subject, for instance by blood, serum, synovial fluid or urine collecting. It can also be obtained, without any limitation, from a cell, tissue, cartilage or synovial fluid.

An individual afflicted with a cartilage disorder and to be tested, tested and/or treated according to any of the methods, uses, assays, kits and other computer systems described herein is a human subject that is a candidate for treatment with an FGF-18 compound, such as sprifermin or a fusion protein comprising an FGF-18 moiety. In a preferred embodiment, the individual has been diagnosed with cartilage disorder, or exhibits a symptom of cartilage disorder. In a further embodiment, the present invention encompasses a kit comprising means for performing the methods described above and instructions for use. Preferably, the kit comprises means for detecting the presence of at least one of the biomarkers according to the invention (e.g. C1M, C3M and/or CRPM) and for quantifying them. The kit may comprises means for detecting the presence of at least two of the biomarkers according to the invention and for quantifying them.

The methods and kits according to the present invention are useful in clinical diagnostic applications. However, as used herein, the term "diagnostic" is not limited to clinical or medical uses, and the diagnostic methods and kits of the invention claimed herein are also useful in any research application, and during clinical trials, for which it is desirable to test a subject for the presence or absence of any markers described herein.

In the context of the invention, the presence of at least one of the biomarkers according to the invention (e.g. C1M, C3M and/or CRPM) and their quantitation may be detected by any technique known per se to the skilled artisan, including ELISA for instance. Other embodiments of the invention within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims that follow the examples.

DESCRIPTION OF THE FIGURES

FIG. 1: Scheme of the dosing regimens used for sprifermin in the FORWARD study.

DESCRIPTION OF THE SEQUENCES

Figure 2:
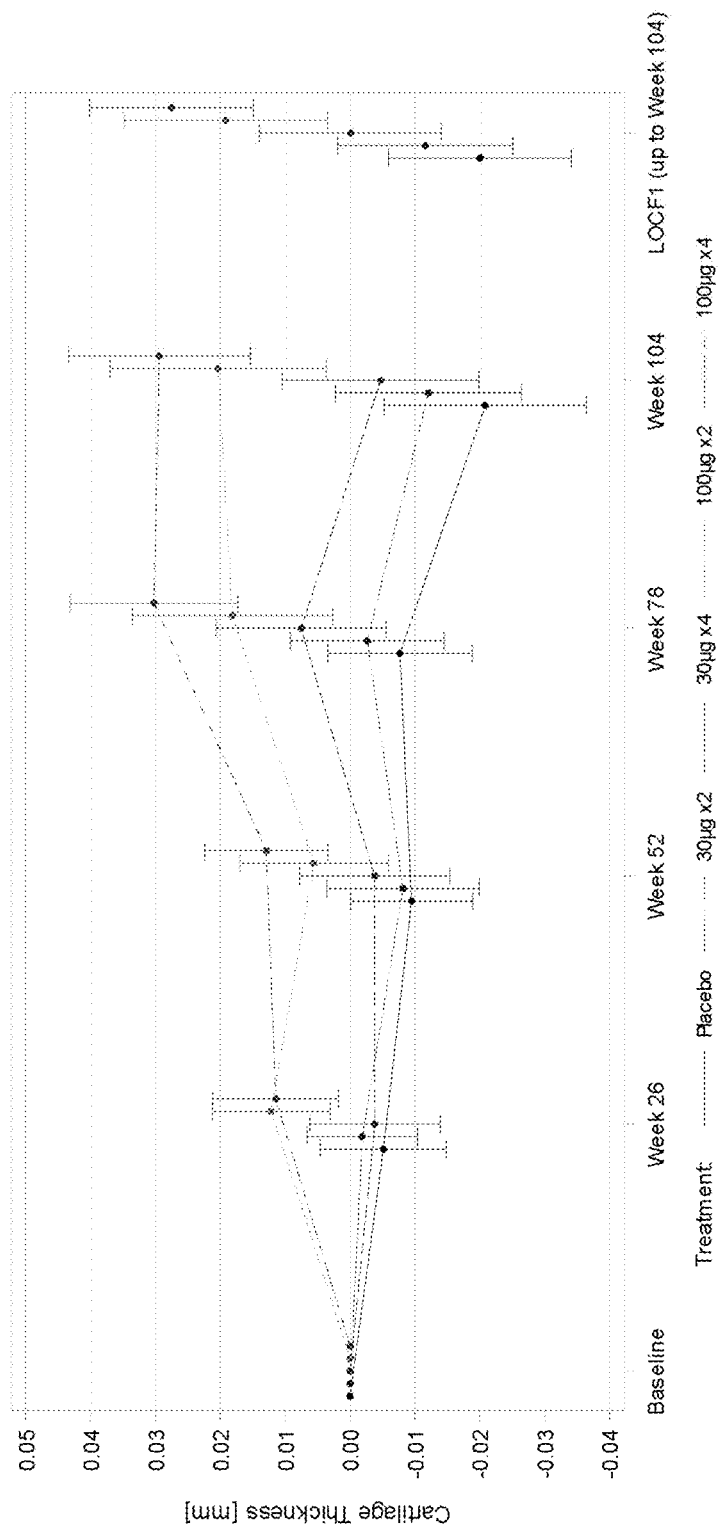
FIG. 2: Mean and 95% CI in Absolute Change from Baseline Over Weeks by Treatment, Cartilage Thickness (mm) in the Total Femorotibial Joint-mITT Analysis Set.

SEQ ID NO. 1: Amino acid sequence of the native human FGF-18.

SEQ ID NO. 2: Amino acid sequence of the recombinant truncated FGF-18 (trFGF-18).

SEQ ID NO. 3: Amino acid sequence of the marker C1M.

SEQ ID NO. 4: Amino acid sequence of the marker C3M.

SEQ ID NO. 5: Amino acid sequence of the marker CRPM.

EXAMPLES

1. Materials and Methods

1.1. FGF-18 Compound

The FGF-18 compound used as a treatment in the present examples is sprifermin. It is a truncated form of FGF-18, as defined in the section "definitions". Two strengths of sprifermin were supplied for the study: 30 μg and 100 μg. Sprifermin was supplied as a white, sterile, freeze-dried powder in 3-mL glass vials. Each vial contained either 31.5 μg or 105 μg of sprifermin active substance; these quantities included a 5% overage, permitting extraction of respectively 30 μg or 100 μg of sprifermin active substance following reconstitution with 0.9% w/v Sodium Chloride Injection (referred to herein as "saline solution"). Excipients of the formulation were sodium phosphate buffer (pH 7.2), sodium hydroxide, 0-phosphoric acid, sucrose, and poloxamer 188. Kits for 30 μg treatments contained 1 glass vial of sprifermin (30 μg strength) and 1 glass ampule of sterile saline solution for injection (2 mL per ampule). Kits for 100 μg treatments contained 1 glass vial of sprifermin (100 μg strength) and 1 glass ampule of sterile saline solution for injection (2 mL per ampule). For all treatment groups, the volume administered was 2 mL.

1.2. Methods

FORWARD Study

The present study was based on the FORWARD study (EMR700692-006). Five groups of patients were studied:

Group 1 (4 cycles placebo; hereafter referred to as placebo): 108 subjects.

Group 2 (2 cycles sprifermin 30 μg/injection alternating with 2 cycles placebo; hereafter referred to as sprifermin/placebo 30 μg): 110 subjects.

Group 3 (4 cycles sprifermin 30 μg/injection; hereafter referred to as sprifermin 30 μg): 111 subjects.

Group 4 (2 cycles sprifermin 100 μg/injection alternating with 2 cycles of placebo; hereafter referred to as sprifermin/placebo 100 μg): 110 subjects.

Group 5 (4 cycles sprifermin 100 μg/injection; hereafter referred to as sprifermin 100 μg): 110 subjects.

According to the FORWARD study, the patients received 4 cycles of treatment (each consisting of 3 once-weekly intra articular injections over 3 consecutive weeks) at intervals of 6 months (see FIG. 1). Injections were all done intraarticular (i.art.).

The primary efficacy endpoint was the change from Baseline in cartilage thickness in the total femorotibial joint as evaluated by MRI at 2 years.

Exploratory endpoints included Baseline protein markers and/or genetic markers associated with response to treatment or disease progression (response assessed by MRI and/or questionnaire).

Inclusion/Exclusion Criteria

The study enrolled adult subjects of either sex with primary femorotibial OA according to American College of Rheumatology (ACR) clinical and radiographic criteria who had Kellgren-Lawrence grades (KLG) of 2 or 3 and a minimum joint space width (JSW) of >2.5 mm in the medial compartment. Subjects must have had pain in the target knee on most days and/or require symptomatic treatment of knee pain with paracetamol (acetaminophen), systemic non-steroidal anti-inflammatory drugs (NSAIDs) including COX inhibitors (COXibs), or tramadol on most days of the previous month, and must have had both: 1) A history of pain due to OA in the target knee for at least 6 months, and 2) Pain score for the target knee of 4 to 9 points in response to Question 1 of the Western Ontario and McMaster Universities Osteoarthritis Index (WOMAC) pain index ("how much pain have you had [in the target knee, over the past 48 hours] when walking on a flat surface?") at screening and Baseline, after washout of at least 5 half-lives of analgesic medication(s): acetaminophen, topical or oral systemic NSAIDS, COXibs, opioids, and/or tramadol. Women of childbearing potential must have used a form of contraception with a failure rate of less than 1% per year throughout the study.

Main exclusion criteria included malalignment of >5 degrees in the femorotibial axis of the target knee, clinical signs of inflammation (i.e., redness) in the target knee, i.art. administration of corticosteroids or hyaluronic acid into either knee within 6 months before screening, any plan for knee surgery (affecting either the target or the contralateral knee) within the next 2 years, concomitant conditions or treatments deemed to be incompatible with study participation, contraindications to MRI scanning (including inability to fit in the scanner or knee coil), pregnancy or breastfeeding, participation in another clinical study within the past 30 days, and legal incapacity or limited legal capacity.

Written informed consent must have been obtained prior to any study-related activity.

Statistical Methods

The treatment effect on the primary endpoint was assessed through dose-ranging using a repeated measurement analysis of variance (ANOVA, using PROC MIXED in SAS) on absolute change from Baseline, including the baseline value, the treatment group, the time, and the country as factors and treatment-by-time point as interaction. The primary efficacy analysis consisted of testing the linear dose relationship and the overall treatment effect at 2 years. The significance level was set at 5% 2-sided for both tests. Pairwise comparisons (sprifermin versus placebo, and between sprifermin dose and regimen groups) were performed within the context of this modelling framework. For each pairwise comparison, the difference between treatments and the corresponding 95% confidence interval (CI) and p-value are presented. The same ANOVA model used for the primary endpoint was used to assess the treatment effect on continuous secondary endpoints such as MRI endpoints, WOMAC endpoints (total, pain, function, and stiffness scores), and X-ray endpoints at each time point and over time. Logistic regression was used to assess the treatment effect on the binary efficacy endpoints such as the OMERACT-OARSI responder rate. Point estimates for each pairwise comparison and corresponding 95% CIs and p-values are provided.

Pain and Function Assessments

The WOMAC is a validated instrument used to assess symptom modification in clinical OA studies. This clinical score was developed in 1981 and is regarded as a valid instrument by both clinical researchers and regulatory authorities. The WOMAC is widely used in clinical studies in hip and knee OA, and has been extensively validated.

Subjects had to answer all of the 24 questions themselves (i.e. 5 for pain, 2 for stiffness and 17 for physical function assessment), using the 11-box NRS assessment (with categories of 0 to 10) with reference to the past 48 hours. Different forms of the questionnaire exist for the right and the left knees: in order to reduce confounding of WOMAC responses by symptoms in the contralateral knee, subjects used the WOMAC questionnaire specific to the target knee. For administration of the questionnaire, instructions for the WOMAC 3.1 Index were followed.

X-Ray Assessment of JSW

Change in JSW as measured by X-ray is a recognized endpoint accepted by the European Medicines Agency and the United States Food and Drug Administration for use in efficacy studies in OA. The JSW was measured using standardized technique.

qMRI Assessment

The primary endpoint for the DBPC treatment phase was the change from Baseline in cartilage thickness in the total femorotibial joint as evaluated by qMRI at 2 years in the mITT. Cartilage thickness of the total femorotibial joint were calculated in 2 ways:

Average Cartilage Thickness (Total Volume divided by Total Surface Area)

Total Cartilage Thickness (sum of cartilage thickness in medial and lateral compartment).

The treatment effect on the primary endpoint was assessed through dose-ranging using a repeated measurement analysis of variance (ANOVA) on absolute change from Baseline, including the treatment group, the time point, and the (pooled) country as fixed factors and the baseline value as covariate and treatment by time point as interaction. Repeated measures over time were accounted for using an "unstructured" covariance pattern.

Pairwise comparisons of absolute change from Baseline in cartilage thickness (sprifermin treatment groups versus placebo) were performed within the context of the modelling framework described above. For each pairwise comparison, the difference between treatments and the corresponding 95% confidence interval (CI) and p-value are presented. P-values (corresponding to Type 3 tests of fixed effects) are reported for all covariates in the original "Overall" model for all time points combined (i.e., baseline value, treatment, time point, treatment-by-time point interaction, country) and for all time points. Estimated coefficients, p-values, and 95% CIs are presented overall and at each time point for (i) the dose relationship (linear trend) and (ii) each pairwise comparison between dose level and placebo.

In order to assess the robustness of the primary results, the tests for linear dose-relationship and for the overall treatment effect were repeated using the PP Analysis Set. For the mITT Analysis Set, a non-parametric analysis was conducted for the ordered data of cartilage thickness in the total femorotibial joint as an alternative method for the primary analysis. Data were ordered by the magnitude of absolute change-from-Baseline over 2 years during DBPC treatment phase using rank transformation.

Biomarkers Measurement

Serological and urine biochemical markers of bone and joint tissue turnover as well as synovial inflammation were evaluated. Potential biomarkers of synovial inflammation included, but were not limited to: neo-epitope of collagen type I degradation (C1M), neo-epitope of collagen type III degradation (C3M), and neo-epitope of synovial C-reactive protein degradation (CRPM). Blood and urine samples for systemic biomarker assessment were collected at the following time points: week 0 (before first injection of sprifermin), week 26, week 54, week 80 and week 104. For time points where injections were also administered, samples were collected before injection. Synovial fluid samples were collected at the time points. These samples were taken just before injection, as part of the i.art. injection procedure and using the same needle that the one used for the injection. For urine collection, second morning void samples were obtained.

The following assessment were made as exploratory endpoints:

Change from Baseline in serum and urine markers associated with administration of the compound.

Baseline protein markers and/or genetic markers associated with response to treatment or disease progression (response assessed by MRI and/or questionnaire).

2. Results

Primary Endpoint (Allcomer)

Total femorotibial joint: A statistically significant treatment effect on the change from Baseline in cartilage thickness in the total femorotibial joint at 2 years was observed (See FIG. 2). Both the sprifermin/placebo 100 µg and sprifermin 100 µg groups showed greater improvements (mean change from Baseline: +0.02 mm and +0.03 mm, respectively) compared with the placebo group (mean change from Baseline: −0.02 mm) at Week 104 ($p<0.001$ for both comparisons). The treatment group difference started at Week 78 in the sprifermin/placebo 100 µg group and Week 52 in the sprifermin 100 µg group. Statistical significance was maintained through Week 104 in both groups. The placebo group showed no improvement from Baseline at any visit through Week 104. There was a statistically significant difference overall (all weeks) for increased cartilage thickness in the sprifermin/placebo 100 µg and sprifermin 100 µg groups, compared with the placebo group ($p=0.002$ and $p<0.001$, respectively). The ANCOVA model was statistically significant for treatment ($p<0.001$), week ($p<0.001$), treatment*week ($p=0.029$), and pooled country ($p=0.009$).

Figure 3:
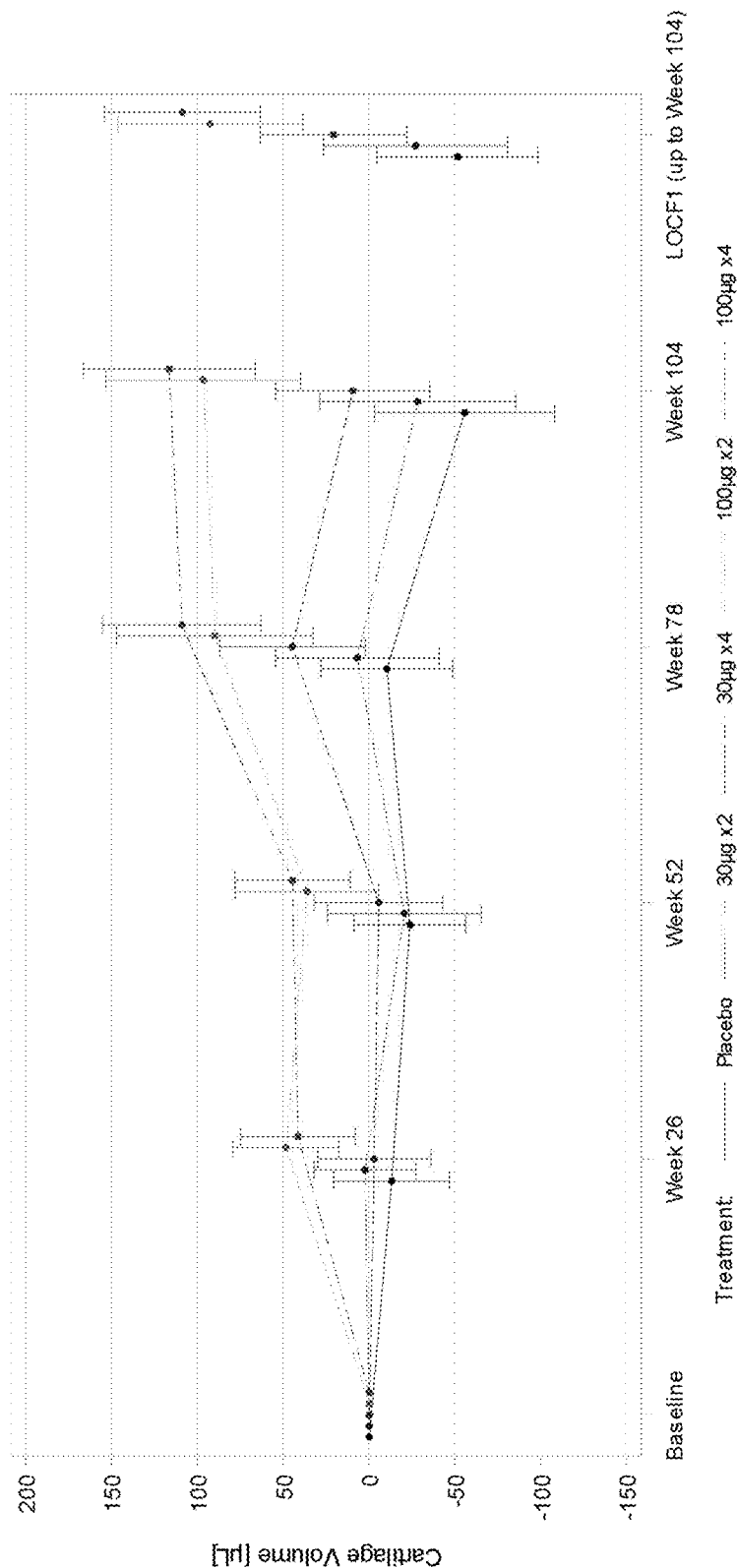
FIG. 3: Mean and 95% CI in Absolute Change from Baseline Over Weeks by Treatment, Cartilage Volume (4) in the Total Femorotibial Joint-mITT Analysis Set.

Cartilage volume in the total femorotibial joint: There was a statistically significant effect of treatment on the change from Baseline in cartilage volume in the total femorotibial joint (FIG. 3; $p<0.001$). The sprifermin/placebo 100 µg and sprifermin 100 µg groups showed greater improvements compared with the placebo group. The statistical significance of sprifermin 100 µg compared with placebo began at Week 78 and persisted through Week 104; the statistical significance of sprifermin/placebo 100 µg compared with placebo appeared at Week 26 and persisted from Week 78 through Week 104. The mean changes from Baseline to Week 104 were −28.2 µL, +9.5 µL, +96.6 µL ($p<0.001$), and +116.5 µL ($p<0.001$) in the sprifermin/placebo 30 µg, sprifermin 30 µg, sprifermin/placebo 100 µg, and sprifermin 100 µg groups, respectively, and −55.54 in the placebo group. There was a statistically significant effect of pooled country ($p=0.011$).

Exploratory Endpoints (biomarkers stratification): The overall objectives of the pharmacodynamic (PD)/biomarker analysis were:

To identify predictive biomarker(s) for identification of patients who retain a positive structural outcome (based on differences in MRI total cartilage thickness with sprifermin versus placebo) while improving symptom outcomes (WOMAC total score and WOMAC pain index score) versus placebo.

To identify predictive biomarker(s) for safety parameters such as AIRs

To characterize functionality biomarkers as potential predictive biomarkers and evaluate potential predictive cut-offs To identify potential prognostic biomarkers (in the placebo group only)

To evaluate biochemical biomarkers as PD biomarkers (e.g., C1M, C3M, CPRM).

Figure 4:
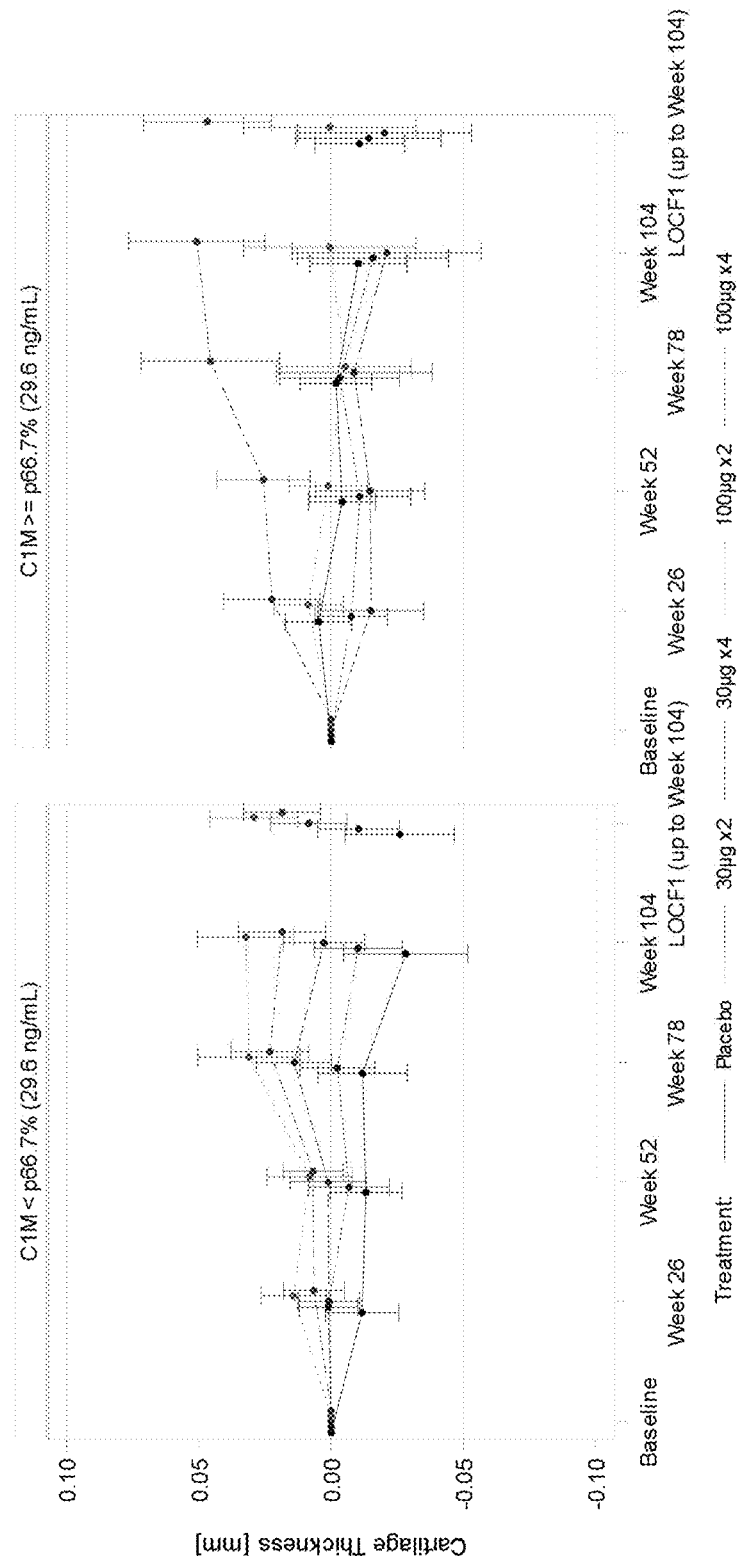
FIG. 4: Mean and 95% CI for Change from Baseline Over Weeks by Treatment and Biochemical Marker of Inflammation, Cartilage Thickness (mm) in the Total Femorotibial Joint-ITT Analysis Set-C1M biomarker.
Figure 5:
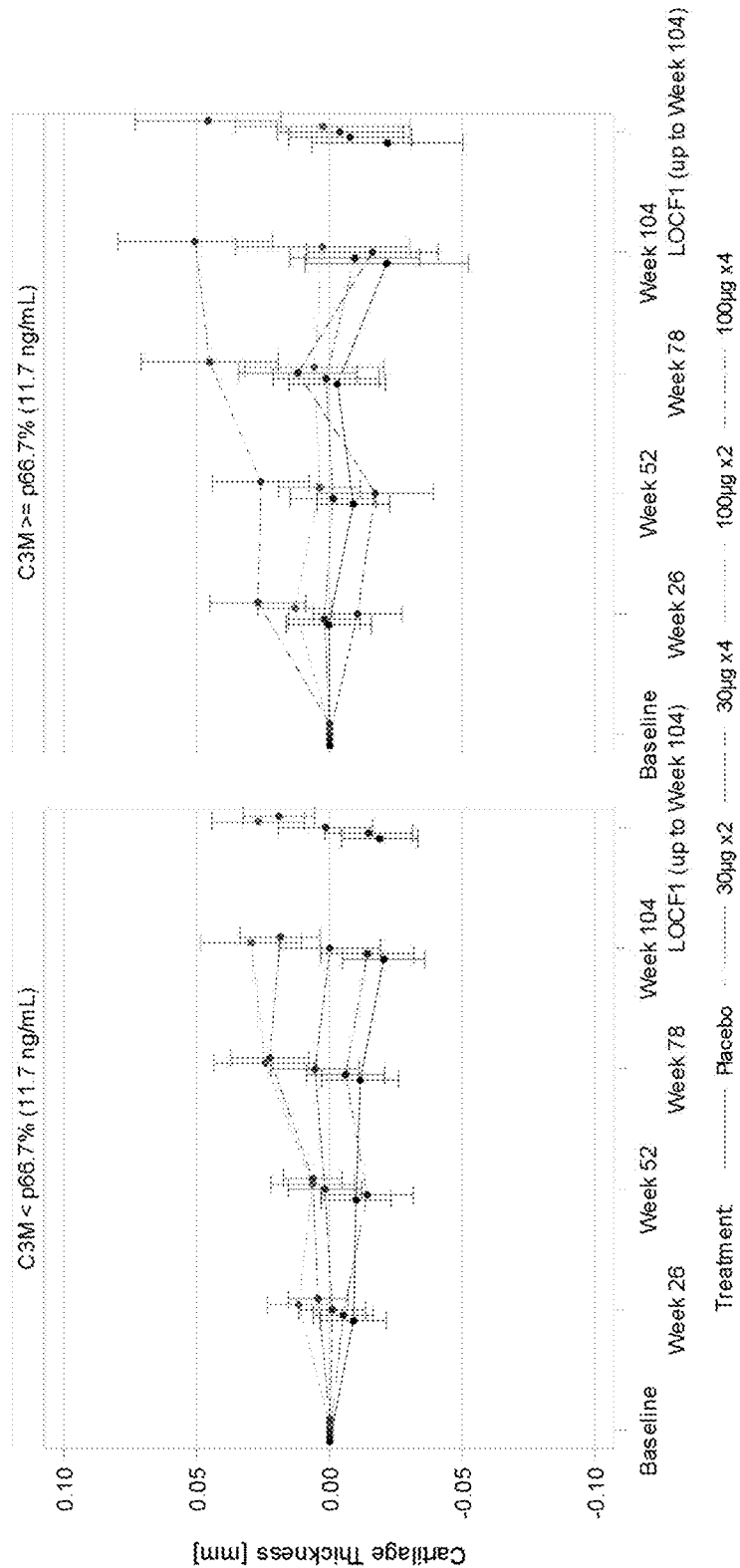
FIG. 5: Mean and 95% CI for Change from Baseline Over Weeks by Treatment and Biochemical Marker of Inflammation, Cartilage Thickness (mm) in the Total Femorotibial Joint-ITT Analysis Set-C3M biomarker.
Figure 6:
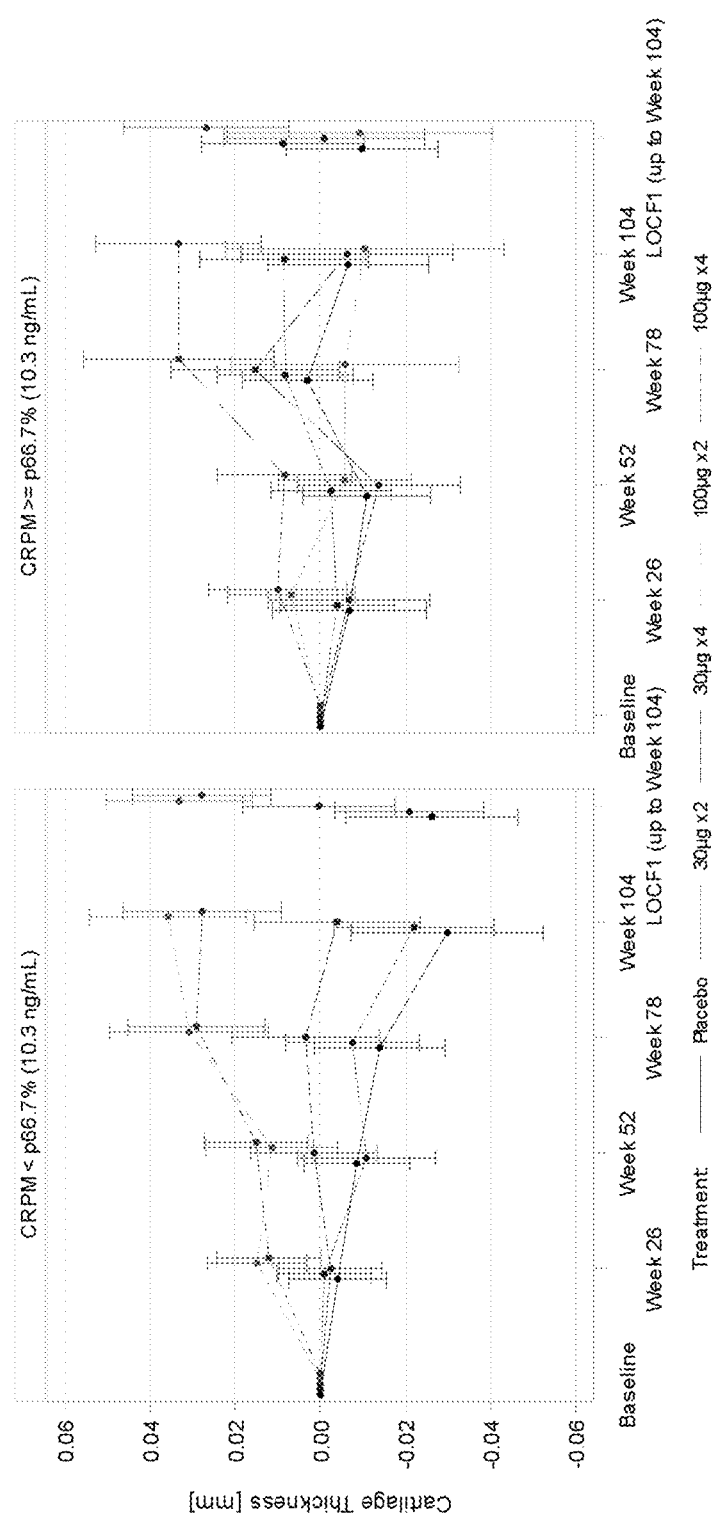
FIG. 6: Mean and 95% CI for Change from Baseline Over Weeks by Treatment and Biochemical Marker of Inflammation, Cartilage Thickness (mm) in the Total Femorotibial Joint-ITT Analysis Set-CRPM biomarker.
Figure 7:
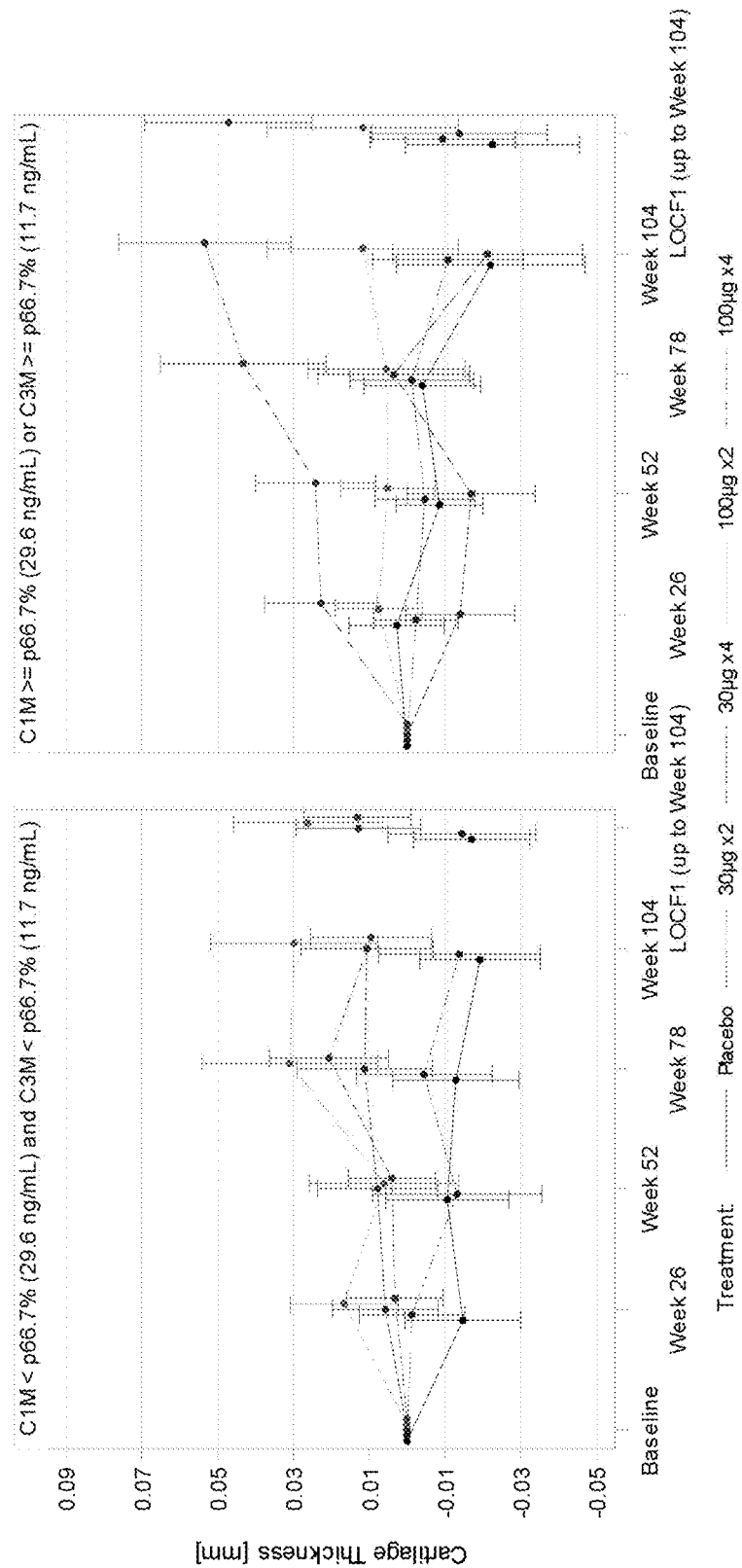
FIG. 7: Mean and 95% CI for Change from Baseline Over Weeks by Treatment and Biochemical Marker of Inflammation, Cartilage Thickness (mm) in the Total Femorotibial Joint-ITT Analysis Set-C1M and C3M biomarker.

Stratification and cartilage thickness in the total femorotibial joint: Changes from Baseline in cartilage thickness in the total femorotibial joint showed the following notable differences between biomarker subgroups at Week 104 (see FIGS. 4-6). Subjects with high levels of inflammatory biomarkers (CRPM, C1M, and C3M) at Baseline did not exhibit a therapeutic effect of sprifermin on total cartilage thickness, except in the sprifermin 100 µg treatment group, four cycles of treatment. Subjects with low levels of inflammatory markers C1M and C3M at Baseline showed a similar improvement in total cartilage thickness compared with allcomers. However, there was a non negligible improvement among subjects with low CRPM levels at Baseline when tread with sprifermin 100 µg treatment groups, either two or four cycles of treatment. These results suggest that high levels of tissue inflammation abolish the therapeutic effect of sprifermin, especially at lower doses. This abolition can surprisingly be counteracted by a more intense treatment with sprifermin, i.e. 100 µg treatment group, four cycles of treatment. This counteraction effect is even stronger when both C1M and C3M biomarkers are used (i.e. a combination of the biomarkers; FIG. 7). Same trend is shown using both C3M/CRPM or C1M/CRPM (i.e. a combination of these biomarkers; data not shown).

Figure 8:
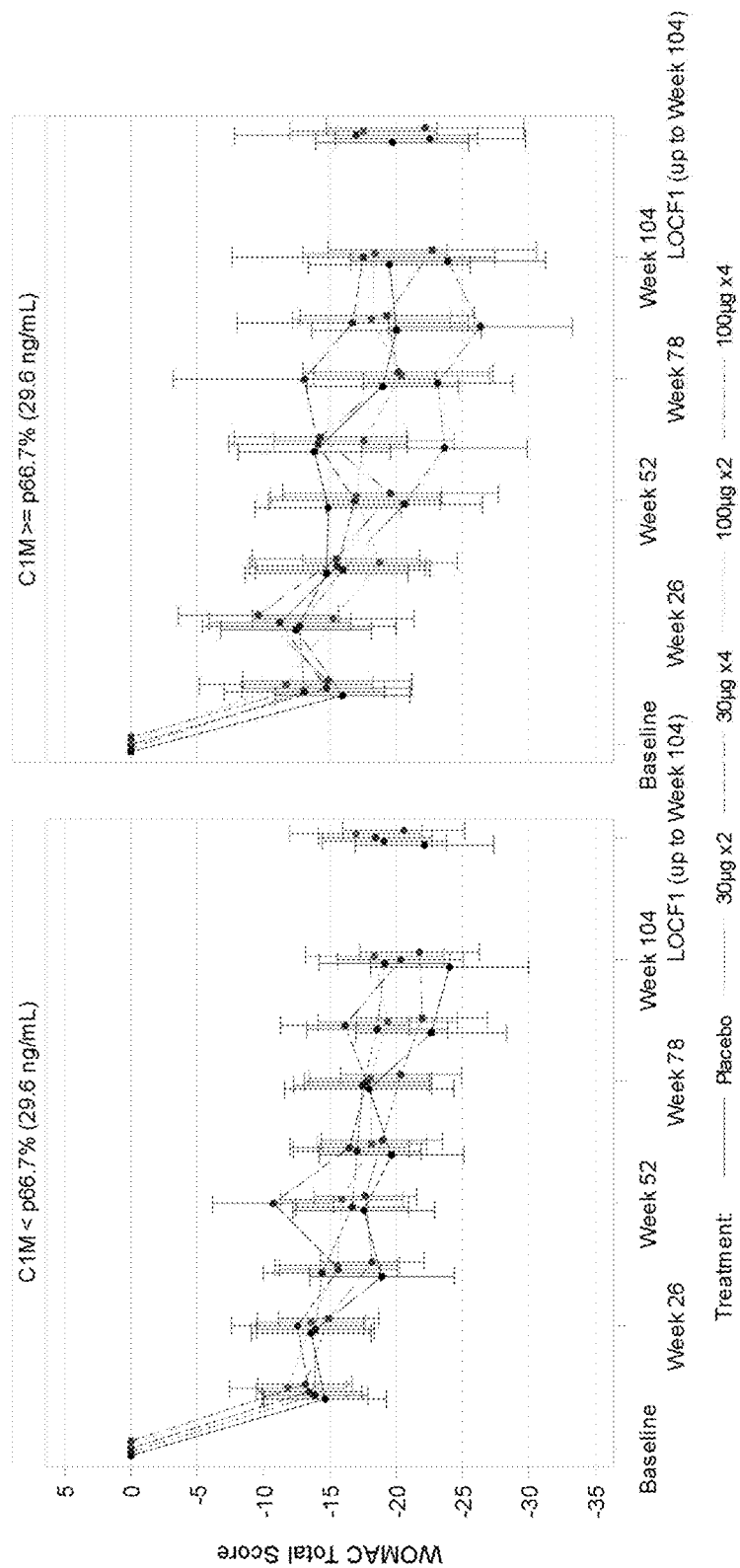
FIG. 8: Mean and 95% CI in Absolute Change from Baseline over Weeks by Treatment and Biochemical Marker of Inflammation Subgroups, WOMAC Total Score in the Target Knee-ITT Analysis Set-C1M biomarker.
Figure 9:
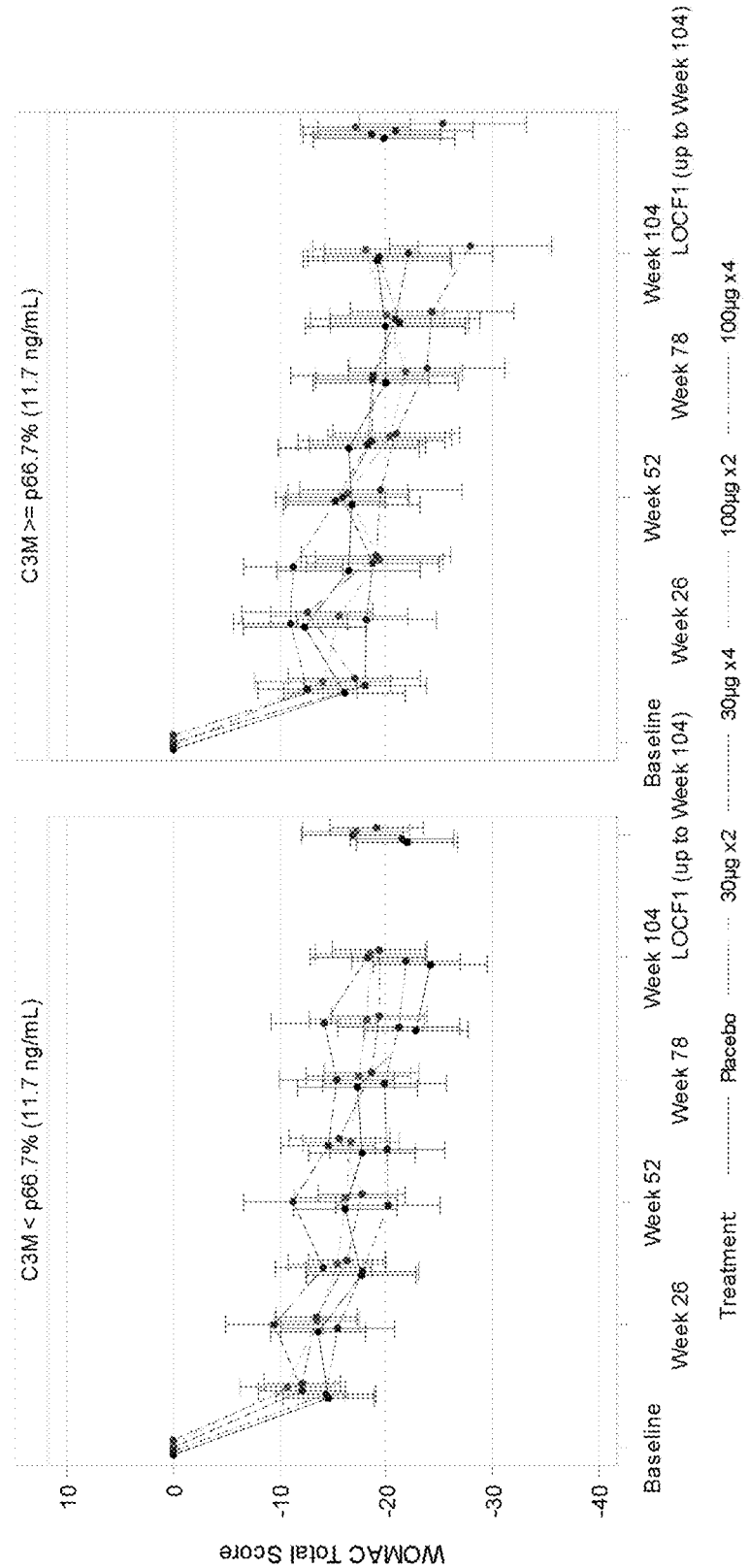
FIG. 9: Mean and 95% CI in Absolute Change from Baseline over Weeks by Treatment and Biochemical Marker of Inflammation Subgroups, WOMAC Total Score in the Target Knee-ITT Analysis Set-C3M biomarker.
Figure 10:
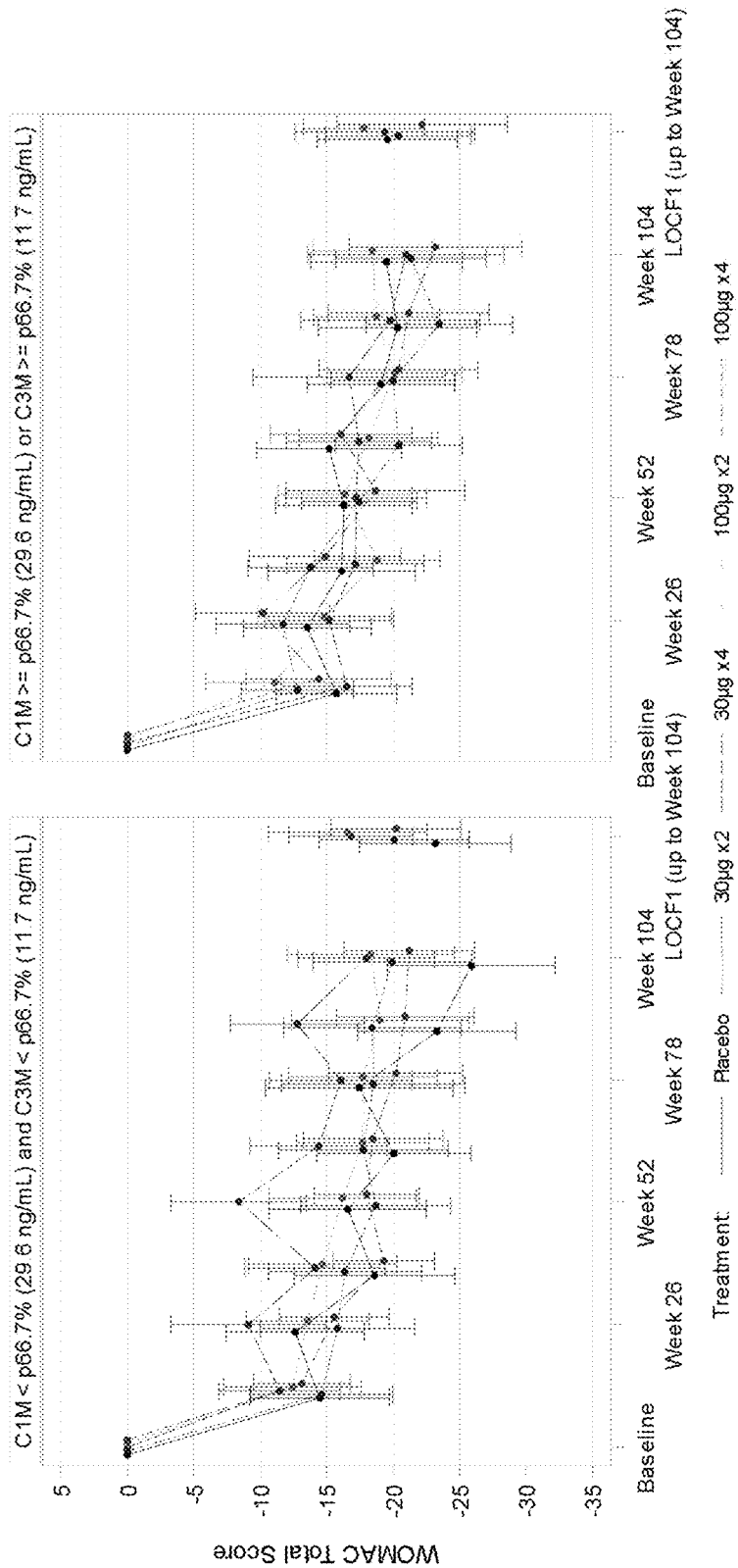
FIG. 10: Mean and 95% CI in Absolute Change from Baseline over Weeks by Treatment and Biochemical Marker of Inflammation Subgroups, WOMAC Total Score in the Target Knee-ITT Analysis Set-C1M and C3M biomarker.

Stratification and WOMAC total scores: Changes from Baseline in WOMAC total scores showed the following notable differences between biomarker subgroups at Week 104. Subjects with lower levels of CRPM biomarker at Baseline globally showed improved outcomes after 104 weeks of treatment with sprifermin (whatever the dosing regimen) for WOMAC total score compared with subjects receiving placebo or with higher levels of biomarkers of cartilage inflammation (data not shown). The results surprisingly show that joints with lower inflammation (low CRPM) not only have a better response to anabolic therapy such as sprifermin with regard to cartilage thickness but also have a positive impact in the WOMAC total scores. In addition, the lower doses, i.e. 2 times 100 µg of FGF-18, or 2 times 30 µg of FGF-18 or 4 times 30 µg of FGF-18 showed no therapeutic efficacy in subjects with high CRPM To the contrary subjects with higher levels of C1M or C3M biomarkers at Baseline globally showed similar outcomes after 104 weeks of treatment with sprifermin (whatever the dosing regimen) for WOMAC total score compared with subjects receiving placebo (FIGS. 8 and 9). The results surprisingly show that chondrocytes with high inflammation (high C1M or C3M) not only have a better response to anabolic therapy such as sprifermin when administered according to an intense regimen with regard to cartilage thickness but also have a positive impact in the WOMAC total scores. This effect is even stronger when both C1M and C3M biomarkers are used (i.e. a combination of the biomarkers; FIG. 10). Same trend is shown using both C3M/CRPM or C1M/CRPM (i.e. a combination of these biomarkers; data not shown).

REFERENCES

WO2008/023063
WO2004/032849
WO2014/023703
WO2006/063362
Hague et al., 2007, Histol. Histopathol., 22:97-105
cartilage.org/files/contentmanagement/ICRS evaluation.pdf
Lotz, 2010, Arthritis research therapy, 12:211
Karsdal, 2016, Osteoarthritis and Cartilage, 24(12): 2013-2021
Ellsworth et al., 2002, Osteoarthritis and Cartilage, 10: 308-320
Shimoaka et al., 2002, J. Bio. Chem. 277(9):7493-7500
Gigout et al., 2017, Osteoarthritis and Cartilage, published online the 18 Aug. 2018 (doi.org/10.1016/j.joca.2017.08.004)
The Merck Manual, 17th edition, page 449
Bellamy et al., 1988, J.Rheumatology, 15:1833-1840
Wolfe, 1999, Rheumatology, 38:355-361
Siebuhr et al., 2014, Osteoarthritis Cartilage, 22(1):44-50.
Saberi Hosnijeh et al., 2016,Arthritis Res Ther. 18:81.
Siebuhr et al., 2013, Arthritis Res Ther., 15(4):R86.
Siebuhr et al., 2016, Biomark Med., 10(2):197-208.
Valdes et al., 2016, Rheumatology (Oxford). 2016 Jun. 2.
Maijer et al., 2016, PLoS One., 11(3):e0149329. eCollection 2016.

ABBREVIATIONS

OA=Osteoarthritis
CI=confidence interval,
DBPC=double-blind placebo-controlled
ICOAP=Measure of Intermittent and Constant Osteoarthritis Pain
ITT=intention-to-treat,
KOOS Symptom Index=Knee Injury and Osteoarthritis Outcome Score symptom index subscale
KOOS QOL=Knee Injury and Osteoarthritis Outcome Score quality of life subscale
LOCF=last observation carried forward,
LFTC=lateral femoro-tibial compartment
MFTC=medial femoro-tibial compartment
mITT=modified intention-to-treat
MOS SF-36=Medical Outcomes Study Short Form-36 General Health Survey
MRI=magnetic resonance imaging
NRS pain score=numerical rating scale pain score
PGA=Patient's Global Assessment
PGIC=Patient's Global Impression of Change
PK=pharmacokinetic
W=Week
WOMAC=Western Ontario and McMaster Universities Osteoarthritis Index.

---

SEQUENCE LISTING

```
Sequence total quantity: 8
SEQ ID NO: 1              moltype = AA  length = 207
FEATURE                   Location/Qualifiers
REGION                    1..207
                          note = human FGF-18
source                    1..207
                          mol_type = protein
                          organism = Homo sapiens
SEQUENCE: 1
MYSAPSACTC LCLHFLLLCF QVQVLVAEEN VDFRIHVENQ TRARDDVSRK QLRLYQLYSR   60
TSGKHIQVLG RRISARGEDG DKYAQLLVET DTFGSQVRIK GKETEFYLCM NRKGKLVGKP  120
DGTSKECVFI EKVLENNYTA LMSAKYSGWY VGFTKKGRPR KGPKTRENQQ DVHFMKRYPK  180
GQPELQKPFK YTTVTKRSRR IRPTHPA                                     207

SEQ ID NO: 2              moltype = AA  length = 170
FEATURE                   Location/Qualifiers
REGION                    1..170
                          note = recombinant truncated FGF-18 (sprifermin)
source                    1..170
                          mol_type = protein
                          organism = synthetic construct
SEQUENCE: 2
MEENVDFRIH VENQTRARDD VSRKQLRLYQ LYSRTSGKHI QVLGRRISAR GEDGDKYAQL   60
LVETDTFGSQ VRIKGKETEF YLCMNRKGKL VGKPDGTSKE CVFIEKVLEN NYTALMSAKY  120
SGWYVGFTKK GRPRKGPKTR ENQQDVHFMK RYPKGQPELQ KPFKYTTVTK             170

SEQ ID NO: 3              moltype = AA  length = 10
FEATURE                   Location/Qualifiers
REGION                    1..10
                          note = recombinant marker C1M
source                    1..10
                          mol_type = protein
                          organism = synthetic construct
SEQUENCE: 3
GSPGKDGVRG                                                         10

SEQ ID NO: 4              moltype = AA  length = 10
FEATURE                   Location/Qualifiers
```

```
REGION                  1..10
                        note = recombinant marker C3M
source                  1..10
                        mol_type = protein
                        organism = synthetic construct
SEQUENCE: 4
KNGETGPQGP                                                                    10

SEQ ID NO: 5            moltype = AA  length = 8
FEATURE                 Location/Qualifiers
REGION                  1..8
                        note = recombinant marker CRPM
source                  1..8
                        mol_type = protein
                        organism = synthetic construct
SEQUENCE: 5
KAFVFPKE                                                                       8

SEQ ID NO: 6            moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 6
KAFVFP                                                                         6

SEQ ID NO: 7            moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 7
KDGVRG                                                                         6

SEQ ID NO: 8            moltype = AA  length = 6
FEATURE                 Location/Qualifiers
REGION                  1..6
                        note = Description of Artificial Sequence: Syntheticpeptide
source                  1..6
                        mol_type = protein
                        organism = synthetic construct
SEQUENCE: 8
KNGETG                                                                         6
```

The invention claimed is:

1. A method for treating a subject having a cartilage disorder characterized by articular cartilage injury or loss of articular cartilage with an FGF-18 compound, comprising the following steps:
   a) determining, from a sample, the quantity of at least one biomarker selected from the group consisting of CIM (Collagen type I degraded by metalloproteinase), C3M (Collagen type 3 degraded by metalloproteinase) and CRPM (C-reactive protein degraded by metalloproteinase), and
   b) administering intraarticularly the FGF-18 compound in an amount that is about 30-100 µg to the subject having lower than 30.0±2SD ng/mL of CIM (Collagen type I degraded by metalloproteinase) and/or lower than 12.0±2SD ng/mL of C3M (Collagen type 3 degraded by metalloproteinase) and/or lower than 10.0±2SD ng/mL of CRPM (C-reactive protein degraded by metalloproteinase),
wherein the FGF-18 compound comprises amino acid residues 28-196 of SEQ ID NO: 1, optionally fused to a heterologous protein or chemical compound.

2. The method of claim 1, wherein the FGF-18 compound is administered in a treatment cycle of once per week for three consecutive weeks.

3. The method of claim 2, wherein the treatment cycle is repeated at least twice.

4. The method of claim 1, wherein the amount of FGF-18 compound is about 30 µg per administration.

5. The method of claim 1, wherein the amount of FGF-18 compound is about 100 µg per administration.

6. The method of claim 1, wherein the FGF-18 compound is sprifermin or sprifermin fused to a heterologous protein or chemical compound.

7. The method of claim 1, wherein the cartilage disorder is selected from the group consisting of osteoarthritis, cartilage injury, fractures affecting joint cartilage or surgical procedures with impact on joint cartilage, and microfracture.

8. A method for treating a subject having a cartilage disorder characterized by articular cartilage injury or loss of articular cartilage with an FGF-18 compound, comprising the following steps:
   a) determining, from a sample, the quantity of at least one biomarker selected from the group consisting of CIM (Collagen type I degraded by metalloproteinase), C3M (Collagen type 3 degraded by metalloproteinase) and CRPM (C-reactive protein degraded by metalloproteinase); and
   b) administering intraarticularly the FGF-18 compound in an amount that is about 30-100 µg to the subject having higher than 30.0±2SD ng/mL of CIM (Collagen type I degraded by metalloproteinase) and/or higher than 12.0±2SD ng/mL of C3M (Collagen type 3 degraded by metalloproteinase) and/or higher than 10.0±2SD ng/mL of CRPM (C-reactive protein degraded by metalloproteinase),
wherein the FGF-18 compound comprises amino acid residues 28-196 of SEQ ID NO: 1, optionally fused to a heterologous protein or chemical compound.

9. The method of claim 8, wherein the FGF-18 compound is administered as a treatment cycle of once per week for three consecutive weeks.

10. The method of claim 9, wherein the treatment cycle is repeated at least twice.

11. The method of claim 8, wherein the amount of FGF-18 compound is about 100 µg per administration.

12. The method of claim 8, wherein the FGF-18 compound is sprifermin or sprifermin fused to a heterologous protein or chemical compound.

13. The method of claim 8, wherein the cartilage disorder is selected from the group consisting of osteoarthritis, cartilage injury, fractures affecting joint cartilage or surgical procedures with impact on joint cartilage, and microfracture.

* * * * *